US009377472B2

(12) United States Patent
Mbebi-Liegeois et al.

(10) Patent No.: US 9,377,472 B2
(45) Date of Patent: Jun. 28, 2016

(54) BIOLOGICAL COMPLEX SPECIFIC FOR ALZHEIMER'S DISEASE DETECTION IN VITRO AND USE THEREOF

(71) Applicants: Amoneta Diagnostics, Huningue (FR); Centre National de la Recherche Scientifique, Paris (FR)

(72) Inventors: Corinne Mbebi-Liegeois, Strasbourg (FR); Jean De Barry, Strasbourg (FR); Francois Sellal, Ammerschwihr (FR)

(73) Assignees: AMONETA DIAGNOSTICS, Huningue (FR); CENTRE NATIONAL DE LA RECHERCHE SCHIENTIFIQUE, Paris (FR)

( * ) Notice: Subject to any disclaimer, the term of this patent is extended or adjusted under 35 U.S.C. 154(b) by 274 days.

(21) Appl. No.: 13/874,052

(22) Filed: Apr. 30, 2013

(65) Prior Publication Data

US 2013/0289140 A1    Oct. 31, 2013

Related U.S. Application Data

(60) Provisional application No. 61/640,436, filed on Apr. 30, 2012.

(51) Int. Cl.
*G01N 33/68* (2006.01)
*C07K 14/47* (2006.01)
*A01K 67/027* (2006.01)

(52) U.S. Cl.
CPC ........ *G01N 33/6896* (2013.01); *A01K 67/0275* (2013.01); *C07K 14/4711* (2013.01); *A01K 2217/072* (2013.01); *A01K 2227/105* (2013.01); *A01K 2267/0312* (2013.01); *G01N 2333/4709* (2013.01); *G01N 2500/10* (2013.01); *G01N 2800/2821* (2013.01); *G01N 2800/50* (2013.01)

(58) Field of Classification Search
CPC .................................................. G01N 33/6896
See application file for complete search history.

(56) References Cited

U.S. PATENT DOCUMENTS

2006/0228349 A1    10/2006    Acton et al.

FOREIGN PATENT DOCUMENTS

| FR | 2940653 | 7/2010 |
|---|---|---|
| WO | WO 2006/014478 | 2/2006 |
| WO | WO 2011/066583 A1 | 6/2011 |

OTHER PUBLICATIONS

Arispe N. et al. (2010) Polyhistidine Peptide Inhibitor of the Aβ Calcium Channel Potently Blocks the Aβ-Induced Calcium Response in Cells. Theoretical Modeling Suggests a Cooperative Binding Process *Biochemistry* 49: 7847-7853.

Bateman D.A. and Chakrabartty A. (2009) Two Distinct Conformations of Aβ Aggregates on the Surface of Living PC12 Cells. Biophys. J. 96: 4260-4267.
Bateman D.A. and Chakrabartty A. (2011) Cell Surface Binding and Internalization of Aβ Modulated by Degree of Aggregation. International J. Alz. Dis. 2011, Article ID 962352, 13 pages.
Bezprozvanny I. (2009) Calcium signaling and neurodegenerative diseases. Trends Mol Med 15(3):89-100.
Brodaty H. et al (2011) The World of Dementia beyond 2020. J Am Geriatr Soc. 59(5):923-7.
Choi SR et al., (2012) Correlation of amyloid PET ligand florbetapin F18 binding with a beta aggregation and neuritic plaque deposition in postmorten brain tissue. Alzheimer Dis assoc Disord Jan. 2012:26(1):8-16.
Chuang JY et al (2012) Interactions between amyoid-beta and hemoglobin:Implication for Amyloid plaque formation in Alzheimer's disease. PLos One;7(3):e33120.
Cizas P. et al. (2011) Prevention of amyloid-beta oligomer-induced neuronal death by EGTA, estradiol, and endocytosis inhibitor. Medicina (Kaunas) 47(2):107-12.
De Barry et al.; (2011) AB142 Binding to Red Blood Cells: A Potential Marker for Alzheimers Disease; Innovative Health Diagnostics; Poster # P 1-075.
Demuro A., et al. (2005) Calcium dysregulation and membrane disruption as a ubiquitous neurotoxic mechanism of soluble amyloid oligomers.J Biol Chem 280(17): 17294-300.
Demuro A., et al. (2010). Calcium signaling and amyloid toxicity in Alzheimer disease. J Biol Chem. 285(17):12463-8.
Gabelle A. et al., (2010) Correlations between soluble α/β forms of amyloid precursor protein and Aβ 38, 40 and 42 in human cerebrospinal fluid. Brain res 1357:135-83.
Georganopoulou DG et al (2005) Nanoparticle-based detection in cerebral spinal fluid of a soluble pathogenic biomarker for Alzheimer's disease. Proc Natl Acad Sci USA. 102(7):2263-4.
Götz J et al . (2012) Tau-targeted treatment strategies in Alzheimer's disease. British Journal of pharmacology;165(5): 1246-59.
Haes AJ et al (2005) Detection of a biomarker for Alzheimer's disease from synthetic and clinical samples using a nanoscale optical biosensor. J Am Chem Soc 127(7):2264-71.
Hardy J. (2002) Testing times for the "amyloid cascade hypothesis". Neurobiol Aging. 23(6):1073-4.
International Search Report from the International Searching Authority (EP) for corresponding International Application No. PCT/IB013/053411 mailed Nov. 8, 2013.
Jack CR Jr et al (2011) Alliance for aging research AD biomarkers work group: Strutural MRI. Neurobiol Aging 32 Suppll: S48-57 Review.
Klein, W.L. et al. (2001) Targeting small Abeta oligomers: the solution to an Alzheimer's disease conundrum? Trends Neurosci 24:219-224.
Klein, W.L. (2002) Abeta toxicity in Alzheimer's disease: globular oligomers (ADDLs) as new vaccine and drug targets. Neurochem Int 41:345-352.

(Continued)

*Primary Examiner* — Amber D Steele
(74) *Attorney, Agent, or Firm* — Hoxie & Associates LLC

(57) ABSTRACT

A biomarker for Alzheimer's disease (AD) comprising a complex of an Aβ amyloid peptide and a cell or a cellular membrane. Non-invasive methods for diagnosing Alzheimer's disease or monitoring its development or progression using this biomarker.

19 Claims, 7 Drawing Sheets

(56) References Cited

OTHER PUBLICATIONS

Klein, W.L. et al. (2004) Small assemblies of unmodified amyloid beta-protein are the proximate neurotoxin in Alzheimer's disease. Neurobiol Aging 25:569-580.

Kuo YM, Kokjohn TA, Kalback W, Luehrs D, Galasko DR, ChevallierN, et al. 2000 Amyloid-beta peptides interact with plasma proteins and erythrocytes: implications for their quantitation in plasma. Biochem. Biophys. Res. Comm. 268, 750-756.

Liegeois et al. (2011) Alteration of AB 1-42 Binding in Red Blood Cells: A Potential Marker for Alzheimer's Disease; Innovative Health Diagnostics; Poster # P 1-137.

Nag S. et al. (2010) Measurement of the Attachment and Assembly of Small Amyloid-Oligomers on Live Cell Membranes at Physiological Concentrations Using Single-Molecule Tools Biophys. J. 99: 1969-1975.

Nag S, et al. (2011) Nature of the amyloid-beta monomer and the monomer-oligomer equilibrium. J Biol Chem. 286(16):13827-33.

Nakagawa et al; "Amyloid-induced Erythrocytic Damage and Its Attenuation by Carotenoids"; FEBS Letters; vol. 585, No. 8, Mar. 28, 2011.

Neniskyte U et al., (2011) Neuronal death induced by nanomolar amyloid $\beta$ is mediated by primary phagocytosis of neurons by microglia. J Biol Chem. 286(46):39904-13.

Poisnel G et al. (2012) PET imaging with [18F]AV-45 in an APP/PS1-21 murine model of amyloid plaque deposition. Neurobiol Aging. 23. [Epub ahead of print].

Ray S, et al. (2011) Tg2576 cortical neurons that express human A are susceptible to extracellular A$\beta$-induced, K+ efflux dependent neurodegeneration. PLoS One.;6(4):e19026.

Selkoe, D.J. (2002) Deciphering the genesis and fate of amyloid beta-protein yields novel therapies for Alzheimer disease. J Clin Invest JID—7802877 110:1375-1381.

Certified Priority Document; U.S. Appl. No. 61/265,340, filed Nov. 30, 2009, 78 pp.

BIOLOGICAL COMPLEX SPECIFIC FOR ALZHEIMER'S DISEASE DETECTION IN VITRO AND USE THEREOF

CROSS-REFERENCE TO RELATED APPLICATIONS

This application is a continuation of U.S. Provisional No. 61/640,436, filed 30 Apr. 2012 which is incorporated by reference in its entirety.

STATEMENT REGARDING FEDERALLY SPONSORED RESEARCH OR DEVELOPMENT (none)

REFERENCE TO MATERIAL ON COMPACT DISK (none)

BACKGROUND OF THE INVENTION

1. Field of the Invention

The present invention relates to a biomarker for Alzheimer's disease (AD) comprising a complex of an Aβ amyloid peptide and a cell or a cellular membrane and to a non-invasive method for diagnosing Alzheimer's disease or monitoring its development or progression using this biomarker.

2. Description of the Related Art

Alzheimer's disease (AD) is a progressive neurodegenerative disorder resulting in loss of memory and cognitive function that disrupts work, hobbies and daily life. This disease is a dementia, progressing over several years from very mild to severe stages. About 35.6 million people worldwide are presently living with dementia; this number should increase to 65 million by 2030 and 113 million by 2050. Indeed, AD is the most common cause of dementia representing 60% to 80% of all dementia cases in adults aged 65 and over (Brodaty et al., 2011), thus imposing significant burdens on the affected individuals and their families as well as economic and social costs on medical and healthcare resources in both developed and emerging countries.

Alzheimer's disease ("AD") is a progressive disease. It is now well recognized that biochemical changes preceding AD may be present in an affected individual up to 20 years before clinical symptoms develop and that physiopathological processes associated with the disease begin many years before the clinical diagnosis is set.

Disease pathology is associated with increased deposits of β-amyloid (Aβ) plaques in the brain as well as with increases in the intracellular aggregates of Tau protein that form neurofibrillary tangles in neurons (Marcus et al., 2011, Gotz et al., 2012). This last event is associated to a progressive neuronal loss.

Currently, there is no single test to detect Alzheimer's disease. Usually only a "potential" diagnosis is made based on a combination of clinical examination, neuropsychological tests, and brain imaging that is conducted over a series of weeks or months. Sometimes detection of biomarkers in cerebrospinal fluid is also performed but this requires a lumbar puncture to obtain a biological sample for assay. Lumbar punctures are often avoided because they are painful and risky to the tested patient. Unfortunately, an accurate diagnosis of AD was often only provided by autopsy, until now.

Conventional tests attempting to diagnose AD faced two important limitations: they lacked the sensitivity necessary for early detection of AD and were unreliable. Diagnosis of Alzheimer's disease was often assessed very late in its progression, for example, 3 to 4 years after a patient's first complaint, thus preventing the initiation of early care and delaying therapy or proper management of the disease and its associated disabilities. Conventional tests were also unreliable since they lacked the specificity and sensitivity necessary to identify subjects having AD, for example, tests measuring amyloid proteins in blood plasma yielded different results depending on the amount of binding of amyloid proteins to blood components or depending on the time of day when a blood sample was obtained. These conventional tests lacked an easily accessible, sensitive and specific biomarker for AD.

This was a major impediment and bottleneck to developing reliable and rapid biochemical tests for the pathologies associated with Alzheimer's disease. Another impediment was the identification of a biomarker that did not require invasive sample collecting, such as a spinal tap.

The lack of such an accessible, sensitive and specific biomarker that could be validated by cellular, animal model, pre-clinical models, and human testing impeded the development of therapies and drugs for AD or for the pathological processes triggering AD or involved in the progression of AD.

Pathological phenomena associated with the development of Alzheimer's disease were known. However, knowledge of these phenomena did not provide accessible, sensitive and specific biomarkers for AD. The underlying neurodegenerative mechanism of AD involves several interacting processes: neuronal death, oxidative stress, abnormal protein processing particularly beta-amyloid production (Aβ) and tau and mitochondrial dysfunction. These processes result in the characteristic accumulation of beta-amyloid plaques, neurofibrillary tangles and synaptic loss, ultimately leading to cerebral atrophy (Selkoe et al. 2002; Terry R D et al., 2006). More precisely the amyloid precursor protein (APP) is hydrolysed to give beta-amyloid peptides (Aβ) of various lengths the prominent species having 42 or 40 amino acids. These highly hydrophobic peptides display a beta sheet structure and are the major constituents of the amyloid plaques in the central nervous system. The Tau protein is associated to the microtubule network inside nerve cells. During the disease course the Tau protein is hyperphosphorylated, it dissociates from the microtubules and forms neurofibrillary tangles.

For research purposes, compounds that specifically interacted with amyloid plaques were developed. When properly labeled with radioisotopes these compounds allowed in vivo imaging of amyloid deposits in human brain and in animal models (Jack et al., 2011; Poisnel et al 2012). However, this methodology required radiolabelling and positron emission tomography, thus restricting its use to investigational or research purposes only. It did not provide a practical way to assess or diagnose a patient for AD. Moreover, brain amyloid deposits are not directly correlated to disease progression (Chuang et al., 2012; Choi et al 2012). Although characteristic neuropathologic changes are described (e.g., accumulation of beta-amyloid plaques and neurofibrillary tangles that begin in the entorhinal cortex and medial temporal lobe and extend gradually to the entire neocortex; Braak et al., 1991), the cause of the disease was not clear (Hardy et al., 2002).

Pathogenesis was also associated with the accumulation of the highly amyloidogenic peptide $A\beta_{1-42}$. More recently increasing evidence accumulated that the cytoxic properties of soluble Aβ peptides (either as monomers or more probably as oligomers) were at the origin of the observed neurodegenerating process (Klein et al, 2001, 2002, 2004; Hardy et al., 2002; Selkoe et al., 2002, 2008). According to these observations the hypothesis was made that the measurement of soluble monomers or oligomers of Aβ would be useful to detect AD and possibly to predict the disease. However, use of these amyloid peptides and their oligomers proved problematic since their levels varied at different times of day and their hydrophobicity caused them to bind to blood components and thus varied their concentrations in blood plasma or serum.

Among available biochemical assays the most commonly used is performed on cerebro-spinal fluid samples and involves immunochemical measurement of amyloid peptides ($A\beta_{1-42}$ and $A\beta_{1-40}$), of the protein tau and its hyper-phosphorylated form (Frankfort et al., 2008; Funke et al., 2009; Gabelle et al., 2010; Rosén et al 2012). This assay however was hindered by the need of a spinal tap to obtain the sample and this procedure is expensive and risky for the patient. These prior assays did not provide a way to non-invasively assess Alzheimer's disease since they required invasive sample collection procedures usually from the central nervous system, such as the collection of CSF by spinal tap as opposed to more accessible samples collected by less risky methods such as the collection of peripheral blood, urine or mucosal secretion.

As mentioned above, blood plasma and serum were known to contain substantial amounts of soluble amyloid peptides and tau protein. Numerous publications described attempts to measure such soluble peptides in blood (for a review see Frankfort et al., 2008). However, attempts to develop a non-invasive assay by measuring Aβ peptides in blood or serum were unsuccessful in producing a reliable and repeated assay. It was difficult to obtain reliable measurements of the amounts or concentrations of Aβ peptides in blood plasma or serum because Aβ peptides are hydrophobic and interact with circulating plasma proteins (Kuo et al. 2000). The repeatability and reliability of assays of Aβ concentration in blood plasma was poor due to observed circadian variations of plasmatic Aβ concentration in rats and in human subjects, which made it difficult to accurately measure Aβ concentration with a diagnostic significance.

In addition to Aβ monomers, Aβ oligomers (also called ADDLs) were considered as potentially relevant biomarkers of Alzheimer's disease (Haes et al. 2005; Georganopoulou et al. 2005) and monoclonal antibodies were developed for diagnostic and therapeutic purposes (Funke, et al., 2009; U.S. 2006/0228349 A1; and WO 2006/014478 A1). However, the reliability and significance of results based on measurement of Aβ oligomer concentration in blood plasma was poor for reasons similar to those for Aβ monomers. The accurate measurement of soluble Aβ oligomers was hindered by their interaction with circulating proteins in blood serum and no correlation was established between plasma or serum concentration of Aβ oligomers and the state of AD.

Other blood tests proposed for assessment of AD included multiparametric tests based on genomic, transcriptomic or proteomic analysis of blood lymphocytes. These multiparametric tests were performed on lymphocytes and relied upon assessment of 50 to even more than 150 different parameters. The number and complexity of these assessments and the often complicated technologies used for such measurements make these tests expensive and require the use of special equipment. Moreover, notwithstanding the complexity and expense, clinicians were reluctant to use such methods for detecting AD among mixed forms of dementia since published data show that the specificity and the sensitivity of these tests (below 78%) were not high enough for such a purpose. Consequently, when attempting to definitively diagnose a patient as having AD, the tests did not meet the expectations and requirements of many clinicians.

Generally, the cellular effects of Aβ application to living cells have been observed with Aβ concentrations in the 0.1 to 1 micromolar range (Arispe et al. 2010; Cizas et al., 2011; Ray et al 2011). These concentrations however are not physiological since soluble Aβ peptides concentrations encountered in healthy control or in pathologic tissues are in the range of 0.1 to 10 nanomolar (Neniskyle et al., 2011; Nag et al., 2005 and 2011). It was previously observed that nanomolar Aβ peptide application had no effect on the $Ca^{2+}$ intracellular concentration in living cells (Demuro et al., 2005; Chin et al., 2006; Bezprozvanny et al., 2009; Demuro et al., 2010). Recent studies suggested that several conformational forms of Aβ peptide can bind to cellular membrane (Suwalsky et al 2009). However no link either chemical or functional had previously been observed between the different forms of Aβ bound to the cellular plasma membranes (Bateman et al., 2009).

An immunological determination of beta-amyloid peptide on blood cells membranes as a biomarker of AD was described by Pesini et al., 2009. In this study, the detection of Aβ was performed by an immunochemical method on a limited number of samples from healthy controls and AD patients. However, no significant discrimination was observed between AD patients and controls. This immunochemical method was not able to discriminate AD patients from healthy control individuals and did not employ the biomarker discovered by the inventors and disclosed herein. Indeed the primary use of an antibody directed against beta-amyloid peptide as performed by Pesini et al (2009) does not allow to detect the biomarker of the present invention, which is the direct detection of the link between high affinity and low affinity binding modes of the beta amyloid peptide to the cellular membrane.

BRIEF SUMMARY OF THE INVENTION

In distinction to the methods described above, the invention employs a new biomarker discovered by the inventors and an assay using this biomarker using samples that can be collected simply, safely, and non-invasively, for example, by collecting a sample of circulating or peripherally available cells like red blood cells (RBCs). The present invention describes a complex comprising an Aβ peptide and a cellular membrane as a sensitive and specific biomarker of AD. This complex can be detected on peripheral cells such as red blood cells, platelets or epithelial cells or cells of the nervous system such as cortical or hippocampal neurons. This marker is also detectable and measurable in cellular and animal models of AD. Since this cellular parameter is directly linked to the physiopathology of the disease and reports on disease progression the present invention describes its application in diagnostic purpose, in treatment monitoring, in preclinical and clinical drug development and in developing new therapeutic pathways. This invention also concerns the methods and the kits for the detection of this biomarker.

The practical applications of this biomarker include the following, not limited, embodiments of the invention.

The complex comprising an isolated Aβ amyloid peptide and a cell or a cell membrane may be formed from an isolated Aβ amyloid peptide comprising at least six contiguous amino acids of Aβ1-42 of a mammalian Aβ amyloid peptide. The sequences of residues 1-42 of human, mouse or rat Aβ amyloid are shown underlined in SEQ ID NOS: 1, 2 and 3 respectively. For example, this complex may comprise at least six contiguous amino acids of Aβ1-42 of mouse or rat Aβ amyloid peptide or at least six contiguous amino acids of Aβ1-42 of human Aβ amyloid peptide. It can be formed from specific Aβ amyloid peptides such as human Aβ1-42, human Aβ1-40, human Aβ10-35, human Aβ17-25 or human Aβ25-35. Other isoforms of Aβ amyloid peptides, such as those containing between 36-43 residues (or any intermediate value in this range) may also participate in complex formation. Aβ amyloid in different conformational states, in monomeric or in multimeric forms, or modified to change its conformational state or to form monomers or oligomers, for example by variation of salt, pH, temperature, or surfactant concentration, may be employed.

This complex may be obtained by incubation of said cell or cell membrane with 0.1 to 2 micromolars of said an isolated Aβ amyloid peptide in a biological fluid or an iso-osmotic medium and at a temperature comprised between 4 and 42° C.

This complex may include an isolated Aβ amyloid peptide that is tagged or labeled with a fluorophore, radioisotope, stable isotope, spin marker, enzyme, conjugated residue, or other detectable marker. There is no particular limitation on the type of tag or label used. Complexes may also contain an Aβ peptide conjugated to another moiety, such as an exogenous protein sequence, such as a His tag or immunogenic carrier.

Use of such a complex to detect, prevent, or treat Alzheimer's disease or a disease or disorder associated with amyloid deposition is also contemplated.

According to another object of the present invention relates to the use of said complex for screening an agent or compound that inhibits the effects of priming for use as a therapeutic agent for Alzheimer's disease or a disease or disorder characterized by amyloid deposits.

The cell or cell membrane component of the complex may comprise an animal cell, such as that of a human or non-human mammal, such as a mouse or rat or a non-mammal cell such as a cell from invertebrate. In some embodiments, an anucleated cell is used, such as mature human red blood cell or platelet. The membrane component of the complex may also be a cellular ghost, a liposome, a synthetic cell, or a synthetic membrane. Other kinds of cells that contain nuclei may also participate in complex formation, such as white blood cells including lymphocytes or other buffy coat cells, cells obtained or derived from the nervous system, such as cell types present in CSF, or cells obtained or derived from the endocrine system, including PC 12 cells that were derived from a pheochromocytoma. Cells responsive to NGF may also be used. Other cells including artificial or modified cells, or their membranes, used to model neurological development, differentiation, or disease phenomena may be used to form complexes with the Aβ amyloid peptides.

Complexes may also include those where the Aβ amyloid peptide is bound at a high affinity to the cell or cell membrane and transiently increases the low affinity binding of beta-amyloid oligomers to said cell or cell membrane compared to an otherwise similar cell to which the Aβ amyloid peptide was not previously bound to at high affinity; and/or that increases the intracellular concentration of calcium in the circulating or peripheral cells of a subject.

These complexes may be formed by contacting a cell or cell membrane with an Aβ amyloid peptide for a time and under conditions sufficient to prime the membrane of the cell. Membrane priming can be detected or determined by exposing the cell to a 0.1 to 2 micromolar concentration of an Aβ peptide that increases the level of intracellular calcium ion concentration in a primed cell to a level higher than that of an otherwise identical unprimed cell not previously contacted with the isolated Aβ amyloid peptide. Since the intracellular calcium concentration triggers metabolic cascades in intact cells it is also possible to detect membrane priming by measuring cellular parameters triggered by calcium such as protein conformation (like protein kinase C), enzymatic activities or calcium triggered ionic channels.

Complexes may also include those where the Aβ amyloid peptide is bound at a high affinity to the cell or cell membrane and transiently increases the low affinity binding of beta-amyloid oligomers to said cell or cell membrane compared to an otherwise similar cell to which the Aβ amyloid peptide was not previously bound to at high affinity; and/or that increases the intracellular concentration of calcium in the circulating or peripheral cells of a subject.

In another aspect, the invention is directed to a composition or kit comprising at least one of:
- one or more reagents for isolating or purifying a cell or cell membrane to which a beta amyloid peptide has or will be bound,
- one or more reagents for incubating the cells or cell membranes with a tagged or labelled beta amyloid peptide or a molecule derived from a beta amyloid peptide, preferably, said reagents including a buffered iso-osmotic solution containing 2-[4-(2-hydroxyethyl)piperazin-1-yl]ethanesulfonate or trishydroxymethylaminomethane or phosphatidic acid or trifluoroacetic acid or ethanol or dimethylsulfoxyde or hexafluoro-isopropanol or several of these compounds,
- one or more reagents for measuring a complex of the labelled beta amyloid peptide or a molecule derived therefrom, with the cell or cell membrane, preferably, said reagents including a buffered iso-osmotic solution containing 2-[4-(2-hydroxyethyl)piperazin-1-yl]ethanesulfonic acid or trishydroxymethylaminomethane or phosphatidic acid or trifluoroacetic acid or ethanol or dimethylsulfoxyde or hexafluoro-isopropanol or several of these compounds,
- a device to detect or quantify the amount of complex formation,
- software for detecting, quantifying or otherwise analyzing complex formation, and/or
- written instructions or a user manual for using the composition or kit to detect or assess the risk of Alzheimer's disease.

Yet another aspect of the invention is a method for detecting the presence of an Aβ amyloid-cell or cell membrane complex comprising:

a) purifying or isolating cells or cell membranes preferably from a biological sample of a subject suspected of having, or at risk of developing, Alzheimer's disease or a disease characterized by deposits of amyloid protein in brain or nervous system, b) contacting the purified or isolated cells or cell membranes with a tagged or labeled Aβ amyloid peptide that comprises at least six contiguous amino acids of Aβ1-42 of a mammalian Aβ amyloid peptide preferably at a concentration comprised between 0.1 and 2 micromolar for a time and under conditions suitable for complex formation, preferably in an iso-osmotic medium and/or at a temperature comprised between 4 and 42° C. and/or during an incubation time comprised between 10 minutes and 3 hours, c) detecting complex formation between the cells or cell membranes and the labeled Aβ amyloid peptide, preferably by measuring tagged or labeled Aβ amyloid peptide bound to said cells or cell membranes.

This method may further comprise step d) comparing the amount of complex formation to the amount of complex formation in a normal subject, in a subject not having Alzheimer's disease, or to a normal control value, and diagnosing the subject as having Alzheimer's disease or as being at risk of developing Alzheimer's disease when complex formation is higher than that in the normal subject, in a subject not having Alzheimer's disease, or in a normal control.

Labeled amyloid peptides usable in this method include those which comprise at least six contiguous amino acids of Aβ1-42 of a mammalian Aβ amyloid peptide, including Aβ amyloid peptides derived from human amyloid precursor protein (SEQ ID NO: 1), rats (SEQ ID NO: 2) and mouse (SEQ ID NO: 3). These peptides may range in length from six, seven, eight, nine, ten, eleven, twelve, fifteen, twenty, thirty, forty or more contiguous amino acid residues or any intermediate value within this range. These include human Aβ1-42 (SEQ ID NO: 4), human Aβ1-40 (SEQ ID NO: 5), human Aβ1-25, human Aβ17-25 (SEQ ID NO: 6) and human Aβ25-35 (SEQ ID NO: 7) or peptides comprising these human peptides or fragments of them having at least six contiguous amino acid residues of these sequences.

The mode of tagging or labelling these peptides is not limited and includes use of a fluorophore (such as a bodipy), radioisotope (i.e., $^3H$, $^{14}C$, $^{35}S$, $^{131}I$, $^{18}F$ etc. . . . ), stable isotope (i.e., $^{13}C$), spin marker (such as a TEMPO residue), enzyme (i.e., peroxydase), conjugated residue (i.e., avidin), or other detectable marker.

The above-described method may employ a mammalian cell or cell membrane, such as a human, primate, rat or murine cell. For example, the method may be practiced with human or non-human animal or a non-human animal modeling human Alzheimer's disease or a human disease involving abnormal or pathological deposition of amyloid.

The cell may be a red or white blood cell, a platelet, an endocrine cell or cell of the nervous system, or another kind of anucleated or nucleated cell, including cell ghosts. Alternatively, membranes derived from such cells may be used including membranes from red blood cells, white blood cells and platelets. For example, the isolated cell may be a PC12 cell, a pheochromocytoma-derived cell, or another cell line used to model neurological development, differentiation or disease phenomena, or a membrane thereof.

The cell or membrane may be primed by contact with an Aβ amyloid peptide for a time and under conditions sufficient to prime the membrane of the cell wherein these conditions are an iso-osmotic medium at a temperature preferably comprised between 4° C. and 42° C. and with a Aβ peptide concentration preferably between 0.1 and 100 nanomolar; and wherein membrane priming is detectable by exposing the cell preferably to a 0.1 to 2 micromolar concentration of Aβ peptide that increases the level of intracellular calcium ion concentration in the primed cell to a level higher than that of an otherwise identical unprimed cell not previously contacted with the isolated Aβ amyloid peptide; or a membrane of said primed cell.

The method may use an Aβ amyloid peptide that is bound at a high affinity to the isolated cell or cell membrane and transiently increases the low affinity binding of beta-amyloid oligomers to said cell or cell membrane compared to an otherwise similar cell or cell membrane to which the Aβ amyloid peptide was not previously bound to at high affinity; and/or that increases the intracellular concentration of calcium in the circulating or peripheral cells of a subject. Preferably, the method above and other methods herein are performed under physiological conditions.

In the methods above, the subject may be human, primate, a non-primate mammal, or other non-human animal. Non-human animals modeling Alzheimer's disease may be employed. The methods above may also purify or isolate cells or cell membranes of such a subject by collecting peripheral cells such as epithelial cells or cells associated with or forming a mucous membrane, or the circulating cells of the subject, such as blood cells or platelets. Cells isolated or derived from the nervous system of the membranes of such cells may be used.

Cells used in the methods described herein may be non-invasively collected from the circulation such as blood cells or peripheral tissues of a subject such as epithelial cells or mucosa cells. These cells may be further purified or isolated from other components of the collected sample. For example, red blood cells may be isolated from the other cellular or non-cellular components of blood.

The AD assessment and assays of the invention may be performed on longitudinally collected samples from the same subject or from a cohort of subjects, such as subjects being treated for Alzheimer's disease or for a disease or disorder characterized by the abnormal or pathological deposit of amyloid.

Still another aspect of the invention involves a method for diagnosing a subject as having Alzheimer's disease or for being at risk of developing or progressing for Alzheimer's disease or a disease or disorder characterized by the deposit of amyloid in the brain or nervous system comprising:

a) purifying or isolating cells or cell membranes preferably from a biological sample of a subject suspected of having, or at risk of developing or progressing to, Alzheimer's disease, b) contacting the purified or isolated cells or cell membranes with a tagged or labeled molecule sensitive to calcium concentration under conditions including an iso-osmotic medium temperature comprised between 4 and 42° C. and an exposure time, which allows said molecule to be loaded inside the cells, c) contacting the purified or isolated cells with an Aβ amyloid peptide that comprises at least six contiguous amino acids of Aβ1-42 of a mammalian Aβ amyloid peptide at a concentration between 0.1 and 2 micromolar for a time and under conditions sufficient for the Aβ amyloid peptide to modulate intracellular calcium concentration preferably, said conditions include an iso-osmotic medium and a temperature comprised between 4 and 42° C., d) detecting the intracellular calcium concentration in the cells contacted with the Aβ amyloid peptide by measuring said tagged or labeled molecule sensitive to calcium concentration, e) comparing the intracellular calcium concentration in the cells to that obtained by an otherwise identical method from sample obtained from a normal subject, a subject not having Alzheimer's disease, or to a normal control value, f) diagnosing the subject as having Alzheimer's disease or as being at risk of developing or progressing for Alzheimer's disease when intracellular calcium concentration is higher than the intracellular calcium concentration determined for the normal subject, subject not having Alzheimer's disease, or normal control value. One way to measure intracellular calcium concentration is by calcium imaging.

A variant of the preceding non-invasive method may be conducted with a tagged or labeled Aβ amyloid peptide and wherein step d) also comprises the detection of complex formation between the cells and the tagged or labeled Aβ amyloid peptide by measuring tagged or labeled Aβ amyloid peptide bound to said cells.

In another aspect the invention pertains to a method for screening an agent or compound that inhibits priming for use as a therapeutic agent for Alzheimer's disease or a disease or disorder characterized by amyloid deposits, comprising a) purifying or isolating cells or cell membranes, b) contacting the isolated cells or cell membranes with an agent or compound to be tested and with 0.1 to 100 nanomolars of an amyloid peptide under conditions sufficient to prime the cell or cell membrane of a control that is not contacted with the agent or test compound, wherein said amyloid peptide comprises at least six contiguous amino acids of Aβ1-42 of a mammalian Aβ amyloid peptide, preferably, said conditions include an iso-osmotic medium and a temperature comprised between 4 and 42° C. and an incubation time between 10 minutes and 24 hours, c) contacting the purified or isolated cells or cell membranes from step b) with a tagged or labeled Aβ amyloid peptide that comprises at least six contiguous amino acids of Aβ1-42 of a mammalian Aβ amyloid peptide at a concentration between 0.1 and 2 micromolars for a time and under conditions suitable for complex formation, preferably, said conditions include an iso-osmotic medium and a temperature comprised between 4 and 42° C., d) detecting complex formation between the cells or cell membranes and the tagged or labeled Aβ amyloid peptide by measuring said tagged or labeled Aβ amyloid peptide bound to said cells or cell membranes, e) comparing the amount of complex formation in the cells contacted with the agent or compound with the amount of complex formation in an otherwise identical control sample that was not contacted with the agent or compound, f) selecting a compound that reduces complex formation compared to the control. An associated embodiment is a compound identified by the methods above, the use of the compound to treat a disease or disorder, such as Alzheimer's disease, characterized or associated with deposition of amyloid. The compound may be used for treating AD or a disease or disorder characterized by amyloid deposition. Generally, this comprises administering the compound identified by the methods above to a subject in need thereof.

Another embodiment of the invention is a method for screening an agent or compound that inhibits the subsequent effects of priming for use as a therapeutic agent for Alzheimer's disease or a disease or disorder characterized by amyloid deposits, comprising a) purifying or isolating cells or cell membranes, b) contacting the isolated cells or cell membranes with an agent or compound to be tested and with 0.1 to 100 nanomolars of an amyloid peptide under conditions sufficient to prime the cell or cell membrane, wherein said amyloid peptide comprises at least six contiguous amino acids of Aβ1-42 of a mammalian Aβ amyloid peptide, preferably, said conditions include an iso-osmotic medium and a temperature comprised between 4 and 42° C. and an incubation time between 10 minutes and 24 hours, c) contacting the purified or isolated cells or cell membranes from step b) with
   (i) a tagged or labeled Aβ amyloid peptide that comprises at least six contiguous amino acids of Aβ1-42 of a mammalian Aβ amyloid peptide for a time and under conditions suitable for complex formation, or
   (ii) a tagged or labeled molecule sensitive to calcium concentration under conditions that preferably includes an iso-osmotic medium temperature comprised between 4 and 42° C. and an exposure time which allows said molecule to be loaded inside the cells and subsequently a concentration of Aβ amyloid peptide sufficient to cause an increase in intracellular calcium concentration of a control cell that was primed but not subsequently exposed to the test agent or test compound, wherein the amyloid peptide comprises at least six contiguous amino acids of Aβ1-42 of a mammalian Aβ amyloid peptide for a time and under conditions suitable for complex formation, d) detecting complex formation between the cells or cell membranes and the labeled Aβ amyloid peptide for (i), or detecting the intracellular calcium concentration of cells for (ii), or detecting any parameter of a signaling cascade triggered by beta amyloid peptide binding or mediated by intracellular calcium (iii);

e) comparing the amount of complex formation in the cells contacted with the agent or compound with the amount of complex formation in an otherwise identical control sample that was not contacted with the agent or compound for (i); comparing the intracellular calcium concentration in the cells to that obtained by an otherwise identical method from sample obtained from a normal subject, a subject not having Alzheimer's disease, or to a normal control value for (ii); or comparing any parameter of a signaling cascade triggered by beta amyloid peptide binding or intracellular calcium (iii), and f) selecting a test agent or test compound that reduces complex formation in (i) compared to the control; or that reduces intracellular calcium concentration in (ii) or changes any parameter of the signaling cascade triggered by beta-amyloid peptide binding or intracellular calcium (iii).

An associated embodiment is a compound identified by the method above, the use of the compound to treat a disease or disorder, such as Alzheimer's disease, characterized or associated with deposition of amyloid.

Within these methods, the cells or cell membranes can be of human origin, of non-human animal origin, or can be cultured cells, which may be primary cultured cells or cells from a cultivated cell line.

Another aspect of the invention involves a method, especially a non-invasive method, for detecting alterations in a cell or a cell membrane of a circulating or peripheral cell induced by Alzheimer's disease or by a disease or disorder characterized by deposition of amyloid comprising:

a) purifying or isolating cells or cell membranes preferably from a biological sample of a subject suspected of having, or at risk of developing, Alzheimer's disease or a disease characterized by deposits of amyloid protein, b) contacting the purified or isolated cells or cell membranes with a tagged or labeled Aβ amyloid peptide that comprises at least six contiguous amino acids of Aβ1-42 of a mammalian Aβ amyloid peptide at a concentration between 0.1 and 2 micromolar for a time and under conditions suitable for complex formation, preferably, said conditions include an iso-osmotic medium and a temperature comprised between 4 and 42° C., c) detecting complex formation between the cells or cell membranes and the labeled Aβ amyloid peptide by measuring tagged or labeled Aβ amyloid peptide bound to said cells or cell membranes; and d) measuring in said isolated cells or cell membranes obtained in step b) a change in the conformation of Protein Kinase C (PKC) or at least one other parameter associated with Alzheimer's disease or a disease or disorder characterized by deposition of amyloid (ERK1/2 activity, GSK-3-beta activity, Tau hyperphosphorylation).

Within the methods described herein, the cells or cell membranes can be obtained from a human subject who has Alzheimer's disease or who is at risk of developing Alzheimer's disease, from a non-human animal subject having or at risk of developing a disease or disorder characterized by amyloid deposition similar to human Alzheimer's disease, from an animal that models human Alzheimer's disease, or from cultured, modified or artificial cells. This method may be employed to detect, diagnose, or evaluate a human for Alzheimer's disease or to detect, diagnose or evaluate a non-human animal or animal model of human Alzheimer's disease.

Another aspect of the invention pertains to the development of an animal model for human Alzheimer's disease comprising:

a) purifying or isolating cells or cell membranes from a biological sample of a test animal, b) contacting said purified or isolated cells or cell membranes with
  (i) a tagged or labeled Aβ amyloid peptide that comprises at least six contiguous amino acids of Aβ1-42 of a mammalian Aβ amyloid peptide for a time and under conditions suitable for complex formation, or
  (ii) a concentration of Aβ amyloid peptide sufficient to cause an increase in intracellular calcium concentration of a control cell that was primed, wherein the amyloid peptide comprises at least six contiguous amino acids of Aβ1-42 of a mammalian Aβ amyloid peptide for a time and under conditions suitable for complex formation, c) detecting complex formation between the cells or cell membranes and the labeled Aβ amyloid peptide for (i), detecting the intracellular calcium concentration of cells for (ii), or detecting any parameter of a signaling cascade triggered by beta amyloid peptide binding or mediated by intracellular calcium (iii), d) comparing the amount of complex formation in the cells contacted with the agent or compound with the amount of complex formation in an otherwise identical control sample that was not primed in (i); or comparing the intracellular calcium concentration in the cells to that obtained by an otherwise identical method from sample obtained from a normal subject, a subject not having Alzheimer's disease, or to a normal control value for (ii); and e) selecting a test animal, which exhibits elevations in complex formation in primed cells compared to the unprimed control in (i); or that exhibits elevations in intracellular calcium concentration in primed cells compared to unprimed cells in (ii) or any parameter of the signaling cascade triggered by beta-amyloid peptide binding or intracellular calcium (iii).

Another embodiment represents a method for diagnosing a subject as having a disease or disorder associated with or characterized by the deposit of amyloid, such as Alzheimer's disease, comprising noninvasively isolating a circulating cell or a peripheral cell of a subject, detecting an alteration in the membrane of said cell compared to a normal cell, and diagnosing the subject as having said disease or disorder when the membrane of the cell is altered compared to the membrane of a normal subject not having said disease or disorder. This method may isolate or purify an anucleated cell for noninvasive testing, such a red blood cell from the peripheral circulation or an epithelial or a cell associated with a mucous membrane. It may also involve measuring alterations in the cell's membrane caused by contact, priming or other exposure to an amyloid peptide or component Other embodiments of the invention include:

One practical application of the invention is a method of using the priming effect on the binding of Aβ peptide on intact cells or cellular membrane preparations as a biomarker to detect Alzheimer's disease (see Examples 3 and 4).

An additional practical application of the invention is a method of following disease progression by measuring the primed Aβ binding on cells or cellular membranes preparations (see Examples 3 and 5).

Since several observations concerning this invention were made on non-pathological cells, another embodiment of the present invention is to use the priming functional effect of low Aβ concentrations to develop and screen new therapeutic agents inhibiting this priming effect.

Another embodiment of the invention is to use the primed Aβ binding on nerve or peripheral human cells or on a membrane preparation thereof for diagnostic or drug development purposes (Example 4).

An embodiment of the invention is to use the primed Aβ binding more specifically on blood cells or a membrane preparation thereof for diagnostic or drug development purposes (see Examples 3, 4 and 5).

Another embodiment of the invention is to use the primed Aβ binding on nerve or peripheral human cells to monitor a therapeutic treatment efficacy.

Another embodiment of the invention is to use the primed Aβ binding on animal nerve or peripheral cells for drug development purposes. This includes non pathologic cells such as primary cultured nerve cells or cells derived from animal models of Alzheimer's disease (treated animals or transgenic strains) (see Example 3 and Example 5).

An additional embodiment of the invention describes the use of cell lines (of human or animal origin) such as PC 12 cell line to measure the primed Aβ binding.

Another embodiment of the invention is to use the primed Aβ binding on cells or on a cellular membrane preparation to characterize a cell line or an animal strain as a model of neurodegenerative disease and more specifically a model of Alzheimer's disease.

An embodiment of the invention is to test the primed Aβ binding on cells or on a cellular membrane preparation using Aβ1-42, Aβ1-40 or any peptide derived from Aβ1-42 of a human, rat or mouse sequence or comprising at least a sequence of 6 amino-acids derived from Aβ1-42, and more specifically any sequence such as Aβ17-25 or Aβ25-35.

An embodiment of the present invention is to test the primed Aβ binding or on cells or on a cellular membrane preparation using a labelled peptide by mean of a fluorophore, a radioisotope or a stable isotope, a spin marker, an enzyme or any conjugating residue.

Another embodiment is to detect the primed Aβ binding or on cells or on a cellular membrane preparation using fluorescence measurement, colorimetry, flow cytometry, immunochemistry or immunofluorescence, radioactivity, NMR, PET or EPR.

An embodiment of the present invention includes the methods and kits for measuring primed Aβ binding to cells or cellular membrane preparations.

Another embodiment of the invention concerns the simultaneous or sequential measurement of another cellular parameter and the combination of this parameter with Aβ binding measurement to cells for diagnosis, therapeutic treatment monitoring or drug development purposes. Preferably, this parameter may be the conformational alteration of PKC in red blood cells.

BRIEF DESCRIPTION OF THE DRAWINGS

FIG. 2(g) quantifies fluorescent intensity for each of 2(a) to 2(f).

DETAILED DESCRIPTION OF THE INVENTION

Figure 1:
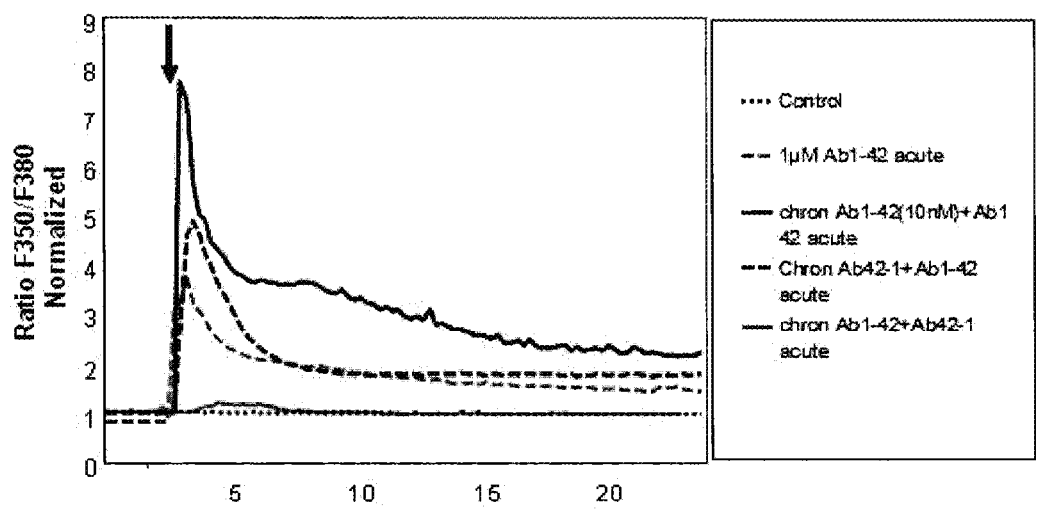
FIG. 1 describes the effect of an acute application of 1 μM $A\beta_{1-42}$ to PC12 cells, which induces an increase in intracellular $Ca^{2+}$ concentration; this is characterized by a transient peak and a long lasting plateau (dashed grey curve). This $Ca^{2+}$ response is enhanced when the cells are preincubated is a low $A\beta_{1-42}$ concentration (10 nM) as show in the black curve: the peak amplitude is increased, and a secondary plateau appears. No effect was observed when the reverse inactive peptide $A\beta_{42-1}$ was used for an acute application on $A\beta_{1-42}$ preincubated cells (dashed black curve) or for preincubation overnight at low concentration (grey curve).

The present invention is based on practical applications of the discovery of a previously unknown cellular effect of $A\beta$ peptide application at physiological concentrations to living cells. In contrast to other observations of $A\beta$ concentrations described in the background section above, the inventors found that an acute application of $A\beta$ at 0.1 to 1 micromolar range induced a transient increase in the intracellular $Ca^{2+}$ concentration. As shown herein a chronic incubation of living cells with nanomolar concentrations of $A\beta$ peptide followed by an acute application of $A\beta$ at 0.1 to 1 micromolar range induces a persistent enhancement of the cellular $Ca^{2+}$ response (see Example 1). This priming effect induced by application of physiological $A\beta$ concentrations makes up the novelty of the invention: it characterizes a functional effect of low $A\beta$ concentrations on living cells. The examples below show that the interaction of nanomolar $A\beta$ peptide concentration with cellular membranes, which are defined as a new biological complex, triggers the binding of $A\beta$ oligomers to the cellular membrane: the binding of $A\beta$ is enhanced following preincubation of the cell with very low $A\beta$ concentrations (see Example 2).

This defines two interacting binding modes of $A\beta$ peptide to the cellular membrane: i) a first high affinity binding mode, which takes place with nanomolar concentrations of and does not alter the intracellular $Ca^{2+}$ concentration; ii) and a low affinity binding mode which concerns $A\beta_{1-42}$ oligomers and is triggered by the high affinity mode. The present invention describes the complex formed by the cellular membrane or part of the cellular membrane and the way to measure it by applying high concentrations of synthetic $A\beta_{1-42}$ peptide or any molecule derived from $A\beta_{1-42}$. Indeed this detection method is mandatory to measure $A\beta$oligomers inserted into the cellular membrane since it relies on a direct and simultaneous interaction of the probe with $A\beta$ endogenous to the biological and lipids constitutive of the cellular membrane.

The inventors disclose herein their discovery of the two modes of binding of $A\beta$ peptide on cellular membranes and their functional consequences, that is, an alteration of intracellular $Ca^{2+}$ concentration. Since an increase of the intracellular $Ca^{2+}$ concentration may lead to cell death, this newly described phenomenon is directly linked to the physiopathology of the disease and may lead to new therapeutic possibilities for Alzheimer' disease.

The methods disclosed herein permit the detection of the first mode binding of the $A\beta$ peptide, described here as a biomarker for Alzheimer's disease by directly measuring the second mode of binding of the peptide. This is achieved using a labelled amyloid peptide or any peptide derived from $A\beta_{1-42}$.

Moreover, the present invention describes a new peripheral biomarker of the disease since the invention applies to peripheral cells and more specifically to blood cells contained in a single drop of blood. This new peripheral biomarker will be used in an in vitro non invasive diagnostic test for Humans. This application of the present invention is a substantial improvement since the only commercially available solution was an immunological measurement of $A\beta$ peptides in cerebro-spinal fluid. This also concerns the procedure simplicity and the detection kits. The biomarker is also very useful in the evaluation of the progression of the disease in AD patients. The biological complex is useful to identify the effect of active drugs, which modify the binding of the $A\beta$ peptide on the cellular membranes of AD patients.

No blood test is commercially available for clinical practice. This is mostly due to the fact that numerous attempts for blood test development involve the measurement of plasmatic or seric $A\beta$ concentrations. Since $A\beta$ is strongly hydrophobic its determination in plasma or serum is problematic and our proposed measurement on red blood cells appears more reliable for several reasons: i) it is not sensitive to interactions with circulating proteins and ii) RBC can behave as an integrator since they are devoid of protein synthesis apparatus hence unable to compensate for exogenous alterations.

Other blood tests currently developed are multiparametric tests based on genomic, transcriptomic or proteomic analysis of blood lymphocytes; to our knowledge measurement of the primed Aβ binding to cell membranes gives the best performance in terms of sensitivity and specificity. It is also simple for interpretation as compared to multiparametric tests. This also contributes to the global novelty of the invention.

The present invention also shows that the primed Aβ binding to cell membranes reports on disease progression, which will allow to follow up patients and to evaluate drug efficacy and to adjust therapeutic dosage. Such a peripheral test easily performed is not yet offered by any company.

To improve the possibilities of the primed Aβ binding to cell membranes as an AD diagnostic method and a disease monitoring biomarker the present invention also shows how it can be combined to the measurement of a complementary biomarker.

Finally the biomarker is directly linked to the physiopathology of AD and its progression and it has been validated in samples from human patients, in cell lines and in animal models reproducing the human disease: these well characterized properties allow its use in preclinical as well as clinical studies for developing new therapeutic agents against Alzheimer's disease. Consequently the use of this new biological marker for drug screening leads to specific companion tests to follow up the efficacy of the candidate of therapeutic agent and follow up in vivo treatment.

EXAMPLES

Example 1

Priming Effect of Low Concentrations of Beta-Amyloid Peptide 1-42 on $Ca^{2+}$ Response Induced in Differentiated PC12 Cells Cell Culture:

PC12 rat pheochromocytoma cells were cultured in RPMI 1640 medium (InVitrogen) supplemented with 5% heat-inactivated horse serum, 10% foetal bovine serum (Dominique Dutcher) and antibiotics (penicillin 100 U/ml, streptomycin 100 U/ml, Sigma) at 37° C. in 5% $CO_2$. PC12 cells were reseeded once a week. Before use, cells were platted in 35 mm glass-bottom culture dishes coated with type I collagen and Poly-L-ornithine; NGF (50 µg/1, Sigma) was added in the culture medium to induce their neuronal differentiation. Cells were used after 5 days in vitro, when they express a complete neuronal phenotype (neurite like extensions, voltage dependent ionic channels, neurotransmitters receptors and neurotransmitter secretion capacities).

Aβ Peptidic Treatment:

$Aβ_{1-42}$ and the $Aβ_{42-1}$ synthetic peptides (Bachem or Anaspec) were first dissolved in Dimethylsulfoxide (Sigma) and then diluted in the working media. According to experimental conditions, two types of peptidic treatments have been applied on the cells. For "chronic" treatment, cells were maintained at 37° C. in 5% $CO_2$ and the treatment consisted of an overnight application of peptide $Aβ_{1-42}$ or $Aβ_{42-1}$ (50 nM final concentration). For "acute" application, $Aβ_{1-42}$ or $Aβ_{42-1}$ were diluted in Hepes buffer pH 7.4 (Hepes 10 mM, D-Glucose 5.5 mM, $MgCl_2$ 1 mM, $CaCl_2$ 2 mM, NaCl 130 mM, KCl 5.4 mM) at 200 nM at room temperature all the recording long for calcium imaging.

Calcium Imaging:

PC12 cells platted on glass-bottom culture dishes were loaded with Fura-2 AM (1 µM, InVitrogen) and pluronic acid (InVitrogen) in a Hepes buffer for 20 min at 37° C. Cells were washed 3 times and again incubated in Hepes buffer for 20 min at 37° C. to ensure complete probe hydrolysis. The culture dish was then placed on an inverted epifluorescence microscope (Nikon). Fluorescence was excited by a xenon lamp equipped with two alternating filters allowing a fluorescence excitation at 350 nm for $Ca^{2+}$-bound Fura-2 and at 380 nm for $Ca^{2+}$-unbound Fura-2. Image pairs were recorded during 20 minutes every 5 seconds using an EM-CCD camera (Hamamatsu Photonics). Emitted fluorescence intensities (510 nm) were measured from regions of interest centered on individual cells. Normalized ratios were calculated. Variations of these normalized ratio reflect $[Ca^{2+}]_i$ changes. No further calibration was performed.

Results:

FIG. 1 describes the effect of an acute application of 1 µM $Aβ_{1-42}$ to PC12 cells, which induces an increase in intracellular $Ca^{2+}$ concentration; this is characterized by a transient peak and a long lasting plateau (pink curve). This $Ca^{2+}$ response is enhanced when the cells are preincubated is a low $Aβ_{1-42}$ concentration (10 nM) as show in the red curve: the peak amplitude is increased, and a secondary plateau appears. No effect was observed when the reverse inactive peptide $Aβ_{42-1}$ was used for an acute application on $Aβ_{1-42}$ preincubated cells (green curve) or for preincubation overnight at low concentration (cyan curve).

Acute application of micromolar $Aβ_{1-42}$ concentrations to differentiated PC12 cells induced an increase in intracellular $Ca^{2+}$ concentration ($[Ca^{2+}]_i$) (FIG. 1). This $[Ca^2]_i$ cellular response was specific for $Aβ_{1-42}$ application since the reverse peptide $Aβ_{42-1}$ had no effect on the cells when applied at µmolar concentrations (FIG. 1). The $Aβ_{1-42}$-induced response was characterized by a rapid increase in $[Ca^{2+}]_i$ followed by a plateau that could last for more than 30 min (FIG. 1).

When the cells were preincubated overnight with low $Aβ_{1-42}$ concentrations (10 nM), the response induced by a subsequent acute application of 1 µM $Aβ_{1-42}$ was amplified (FIG. 1). This enhanced response was characterized by a high peak amplitude and an intermediary plateau following the initial peak (FIG. 1). This priming effect due to cell preincubation was specific for $Aβ_{1-42}$ since preincubation of the cells with the reverse peptide $Aβ_{42-1}$ did not induce a significant change in the $[Ca^{2+}]_i$ response (FIG. 1).

Conclusion:

This example shows that $Aβ_{1-42}$ applied at low concentration does not significantly change the intracellular $Ca^{2+}$ concentration whereas high $Aβ_{1-42}$ concentration induces a strong variation of the $Ca^{2+}$ concentration. A chronic application of 10 nM $Aβ_{1-42}$ induces a priming effect of this response by increasing the peak response, the plateau level and its duration. This effect was not yet described.

Example 2

Increase of $Aβ_{1-42}$ Oligomers Binding to PC12 Cells Following Preincubation of the Cells with Low Concentrations of $Aβ_{1-42}$ Monomers Immunocytochemistry:

In an attempt to characterise the tertiary form of the peptide bound to the cells and responsible for the priming effect that was observed immunocytochemical experiments were performed: PC12 cells were plated on poly-L-ornithine coated coverslips and maintained for 5 days in culture media supplemented with NGF to induce neuronal differentiation at 37° C. According to experimental conditions, PC 12 cells have undergone a chronic treatment and/or an acute treatment (see Example 1). Cells were subsequently rinsed to eliminate unbound Aβ and fixed with 4% paraformaldehyde in phosphate buffered saline (PBS) for 10 minutes. PC12 cells were then incubated in a blocking solution (3% Bovine Serum Albumin in PBS) for 1 hour at room temperature. A rabbit polyclonal antibody A11 (Millipore) directed against Aβ oligomers diluted 1:1500 in blocking solution was applied to the cells overnight at 4° C. Cells were washed three times for 10 minutes with the blocking solution and incubated with the appropriate secondary Dylight 549-conjugated antibody goat anti-mouse, (Jackson Immunoresearch, diluted 1:2000) for 2 hours at room temperature, washed 3×10 minutes in PBS and mounted in Mowiol. Glass slides were observed with an inverted epifluorescence microscope and images were acquired with a digital camera.

Results:

Living PC12 cells were preincubated and/or incubated with different $A\beta_{1-42}$ concentrations. They were then washed and fixed and the amyloid peptide was revealed by fluorescence immunochemistry using an antibody against the oligomeric form of $A\beta_{1-42}$ and the results are illustrated in FIGS. 2(a)-2(f).

Experimental conditions were: panel A, control baseline without $A\beta_{1-42}$; panel B, acute application of 200 nM $A\beta_{1-42}$ for 10 min; panel C, chronic incubation with 5 nM $A\beta_{1-42}$ for 18 hours; panel D, preincubation overnight with 5 nM $A\beta_{1-42}$ followed by acute application of 200 nM $A\beta_{1-42}$ for 10 min; panel E, chronic incubation with 5 nM $A\beta_{42-1}$ for 18 hours; panel F, incubation with 5 nM $A\beta_{1-42}$ for 18 hours followed by acute application of 200 nM $A\beta_{42-1}$ for 10 min. Note in panel C an increase in the fluorescence density indicating an increase in $A\beta_{1-42}$ oligomers binding to the cells. Thus, the priming effect induced by preincubation with physiological $A\beta_{1-42}$ concentration is correlated to an increase in $A\beta_{1-42}$ binding. Panel G of FIG. 2(g) represents the quantification of the fluorescence intensity in the different experimental conditions in 2(a) to 2(f).

Figure 2:
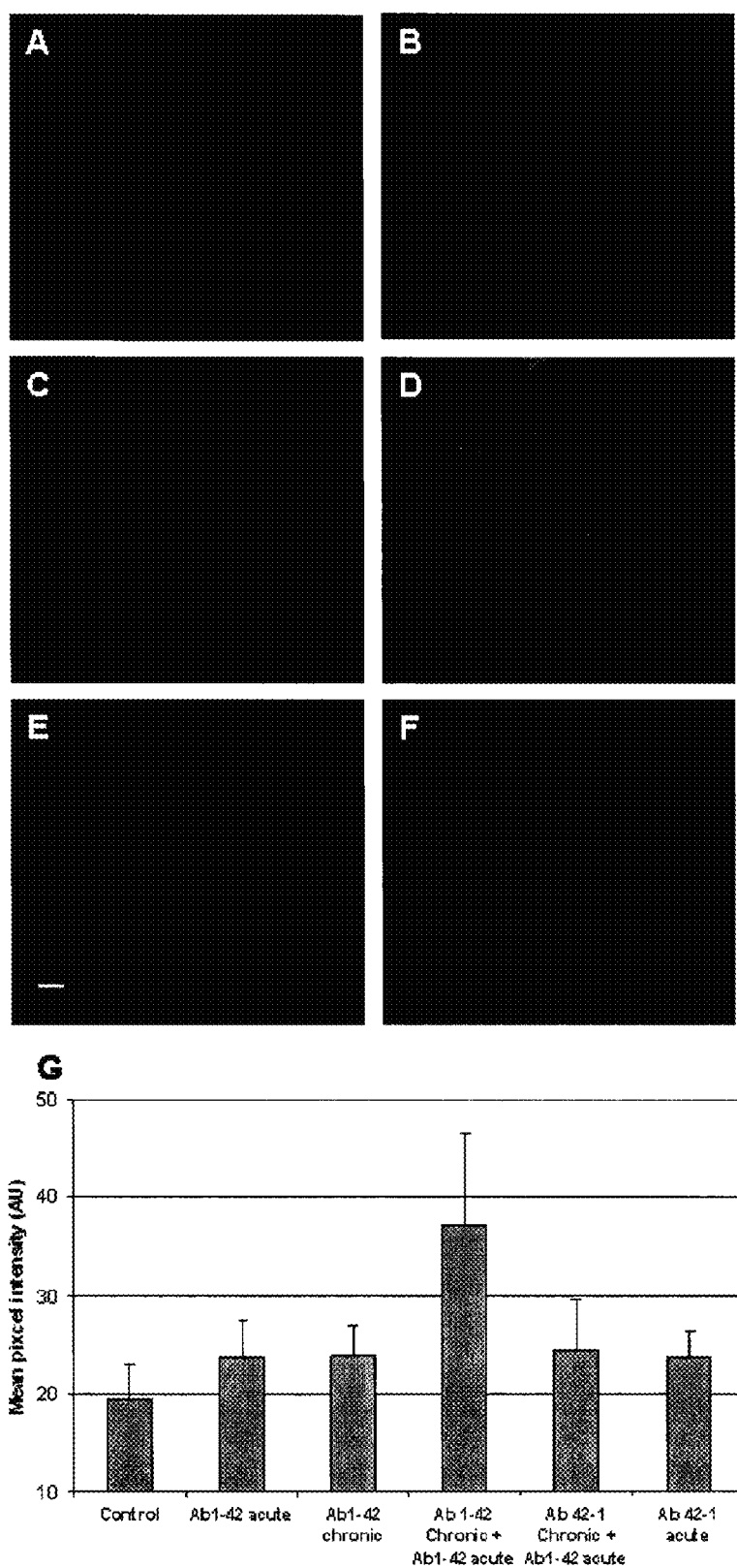
FIGS. 2(a)-2(g). Living PC12 cells were preincubated and/or incubated with different $A\beta_{1-42}$ concentrations. They were then washed and fixed and the amyloid peptide was revealed by fluorescence immunochemistry using an antibody against the oligomeric form of $A\beta_{1-42}$ and the results are illustrated in FIGS. 2(a)-2(f).

No significant fluorescent signal was observed after preincubation with 10 (not illustrated) or 50 nM $A\beta_{1-42}$ (FIG. 2, panel C) or even after acute application of 1 μM $A\beta_{1-42}$ (FIG. 2, panel B). When chronic preincubation was associated to acute stimulation a clear signal was observed (FIGS. 2(d) and 2(g)). Control experiments performed by chronic application of the reverse peptide $A\beta_{42-1}$ did not show any significant primed binding of $A\beta_{1-42}$ oligomers.

Conclusion:

This experiment shows that most of $A\beta_{1-42}$ bound to the cell membranes is oligomeric. This also shows that most these $A\beta_{1-42}$ oligomers only bind to the cell once the membrane is saturated with $A\beta_{1-42}$ monomers at low concentration. Hence, the application of physiological concentrations of $A\beta_{1-42}$ on the cells contributes to increase the capacity of these cells to bind exogenously applied high concentrations of $A\beta_{1-42}$ Example 3

Assessment of Disease Progression in an Animal Model of Alzheimer's Disease

To screen a population at risk of AD or to follow up AD patients during the course of the disease, our aim was to find an index by measuring a new fluorescent probe specific for $A\beta_{1-42}$ to evaluate the amount of bound $A\beta_{1-42}$ on RBC. This index must be constant in time, stable and independent of the instrumentation and of the measurement procedure. For this purpose a fluorescent probe derived from $A\beta_{1-42}$ was used, which is sensitive to changes in its polar environment: when interacting with a lipid membrane or with Aβ oligomers inserted in a cellular membrane the fluorescence spectrum of this probe is modified and reveals bound Aβpeptide.

Methods:

A transgenic mouse strain called TAS/TPM and overexpressing two human genes coding respectively for a mutated amyloid precursor protein (K670N and M671L) and for a mutated form of the human presenilin 1 (M146V) was used (Howlett et al., 2004; Pardon et al., 2009) together with C57BL/6J control mice.

This strain displays a disease similar to the human Alzheimer's disease: the animals start to show amyloid deposits in their brain from the 6th postnatal month to reach a maximum at 20 months. The mice were classified as wild type (C57/B16 controls animals) and double transgenic mice. They were all female. Eight groups were formed as described in the following table:

TABLE 1

Size of the different mice groups involved in example 4.

| | 4 months | 9 months | 14 months | 20 months |
|---|---|---|---|---|
| Wild type | 10 | 21 | 8 | 18 |
| TAS/TPM | 10 | 14 | 12 | 14 |

A 100 μL blood sample was obtained from each animal under slight anaesthesia by retro-ocular puncture. The samples were immediately diluted (1:30) in buffer (NaCl 150 mM; $Na_2HPO_4$ 5 mM; Glucose 1 mM; $CaCl_2$ 0.5 mM pH 7.4) and washed.

Purified RBCs were then incubated for 30 min with 100 nM A1, a specific fluorescent probe consisting of $A\beta_{1-42}$ labeled on lysine 16 with a Bodipy residue previously described by patents FR0859098 and FR0807473. This fluorescent residue is sensitive polarity changes and upon binding of the probe to the cellular membrane the change in the polarity of the environment induces a deformation of the spectrum that is reported by the calculation of a spectral index as described below.

After this incubation period the fluorescence of the samples was measured on a spectrofluorimeter (Horiba) for the mice groups aged 4 and 14 months. Fluorescence spectra were recorded (EX: 480 nm; EM: 495-600 nm) and further analyzed by a gaussian deconvolution using the Peakfit analysis software. The ratio between Gaussian 1 amplitude (centered at 512 nm) plus Gaussian 2 amplitude (centered at 523 nm) on the Gaussian 3 amplitude (centered at 548 nm). This ratio reports on the spectral changes of the fluorescence upon binding of the probe to the cellular membrane.

Figure 3:
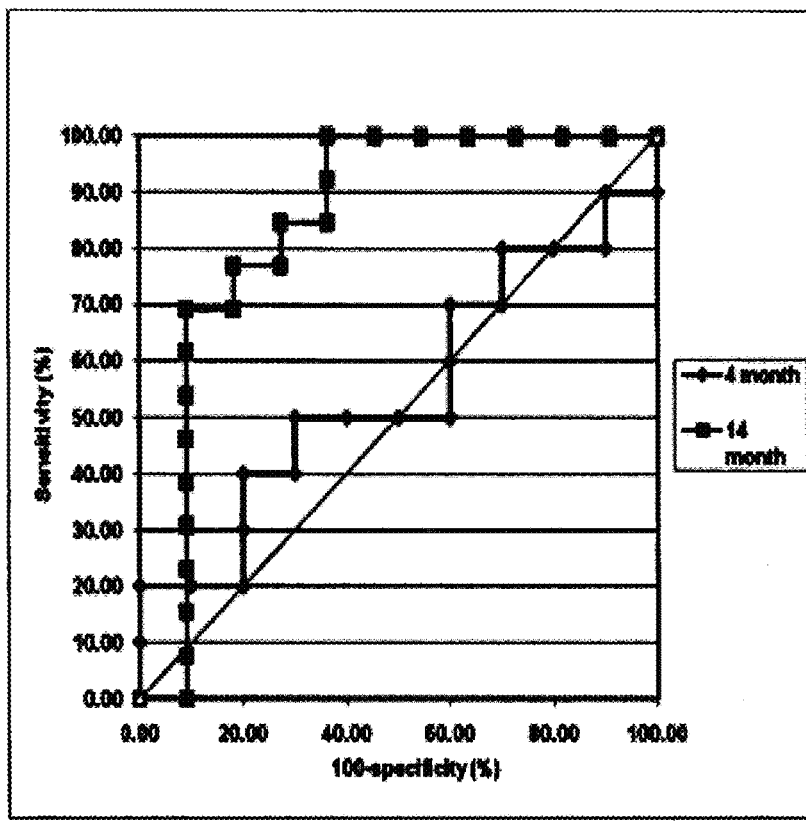
FIG. 3 shows the ROC curves obtained for wild type (WT) and TAS/TPM mice at 4 months and at 14 months. Using this test procedure no significant discrimination was observed between WT and TAS/TPM mice at 4 months, when the amyloid deposit is not yet observed in the brain of the transgenic animals (Howlett D R et al., 2008). In animals aged 14 months, a partial discrimination was obtained. Table 2 summarizes the values of sensitivity and specificity of the test.

Results:

FIG. 3 shows the ROC curves obtained for wild type (WT) and TAS/TPM mice at 4 months and at 14 months. Using this test procedure no significant discrimination was observed between WT and TAS/TPM mice at 4 months, when the amyloid deposit is not yet observed in the brain of the transgenic animals (Howlett D R et al., 2008). In animals aged 14 months a partial discrimination was obtained. Table 2 summarizes the values of sensitivity and specificity of the test.

TABLE 2

Characteristics of the ROC curve illustrated in FIG. 3.

| Age | 4 months | 14 months |
|---|---|---|
| Sensitivity: | 50% | 85% |
| Specificity: | 70% | 73% |
| Area under curve: | 55% | 85% |

The samples from the groups aged 9 or 20 months were analyzed on a flow cytometer (Quantalab, Beckman). The counted cells were gated to eliminate cellular debris and the fluorescence was measured in two separate channels at 520±10 nm and at 550±10 nm. In this case, there was no calculation of a spectral index; the percentage of the cells emitting in both channels was measured.

Figure 4:
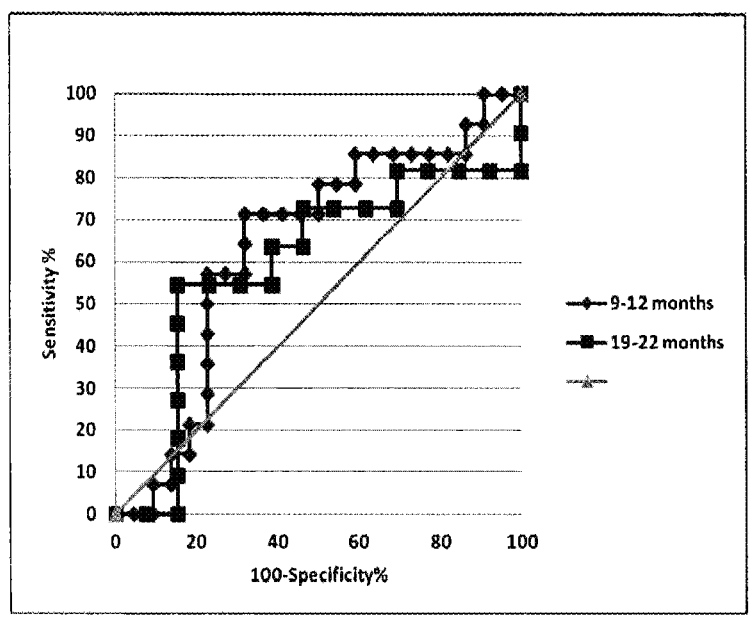
FIG. 4 shows ROC curves obtained for wild type (WT) and TAS/TPM mice at 9 months and at 20 months. In this case, an abundant amyloid deposit is already observed in the brain of 9 month old transgenic animals. Indeed a slight discrimination between WT and transgenic mice aged 9 months was obtained. Moreover, the discrimination between the two groups of 20 month old mice was more prominent especially considering specificity. Table 3 summarizes the values of sensitivity and specificity of the test when flow cytometry is used.

FIG. 4 shows ROC curves obtained for wild type (WT) and TAS/TPM mice at 9 months and at 20 months. In this case, an abundant amyloid deposit is already observed in the brain of 9 month old transgenic animals. Indeed a slight discrimination between WT and transgenic mice aged 9 months was obtained. Moreover, the discrimination between the two groups of 20 month old mice was more prominent especially considering specificity. Table 3 summarizes the values of sensitivity and specificity of the test when flow cytometry is used.

TABLE 3

Characteristics of the ROC curve illustrated in FIG. 4.

|  | 9-12 months | 19-22 months |
|---|---|---|
| Cut off | 2% | 2% |
| Sensitivity | 71.4% | 64.3% |
| Specificity | 52.3% | 83.3% |
| Area under curve | 54.7% | 67% |

Conclusion:

This example shows that it is possible to detect Alzheimer's disease in a mouse model of the pathology by measuring Aβ binding on peripheral cells, namely red blood cells. For this purpose a fluorescent probe derived from $A\beta_{1-42}$ with a bodipy fluorophore was used with two different technical platforms: spectrofluorimetry and flow cytometry, giving comparable results.

Example 4

Discrimination Between Healthy Volunteers and Alzheimer's Patients

Methods:

Measurements were performed on 58 AD patients (46 females and 12 males; 82.6±8.18 years) suffering from mild to severe dementia and 32 healthy controls (26 females and 6 males, 82.9±5.5 years). All healthy controls were given no medication interfering with cognitive function; they had no neurological or psychiatric history. AD patients were recruited using National Institute of Neurological and Communicative Disorders and Stroke and the Alzheimer's disease and Related Disorders Association (NINCDS-ADRDA) criteria for probable AD (McKhann G et al., 1984). Additionally, measurements were performed on patients suffering from multiple sclerosis, which was not dementia: 18 patients suffering from Multiple sclerosis (42.6±13.3 years) were selected.

Blood samples were drawn into 5 ml tubes containing 10 USP units of heparin and kept at 4° C. The blood was centrifuged (2,500 rpm, 5 min) to take off the buffy coat and the plasma. The resulting pellet was washed three times in RBC buffer (TpRBC: NaCl 150 mM; $Na_2HPO_4$ 5 mM; Glucose 1 mM; $CaCl_2$ 0.5 mM pH 7.4) at room temperature. (dilution 1/30)

After the third wash, cells were diluted (1/30) with TpRBC buffer. An aliquot of RBC was loaded with the fluorescent amyloid probe A1 as described in example 4 (bodipy-$A\beta_{1-42}$ final concentration 100 nM) at room temperature for 30 min. The emission spectra were recorded as the mean of 2 scans between 495 and 600 nm (Excitation at 480 nm).

After subtraction of the baseline the resultant fluorescence spectra were deconvoluted as described above in example 4 and a spectral index value was calculated.

The hypothesis AD versus non AD was tested. Five explanatory variables were recorded together with the spectral index value and a downward logistic regression modeling was performed. The specificity and the sensitivity of the measurement method were assessed by Receiver Operating Characteristic Curve (ROC) curves.

Results:

As illustrated in FIG. 1 a fluorescence change of the probe in AD samples was observed. To quantify this change a spectral index was calculated, which involves a Gaussian deconvolution of the fluorescence spectrum into four Gaussian curves and calculating the ratio of Gaussian 1 and 2 over Gaussian 3. An increase in the spectral index measured in the presence of Red Blood Cells (RBC) reveals the pathology. This methodology was then applied to the samples obtained from the selected participants.

Two groups were considered for statistical analysis: non AD and AD individuals. A first regression analysis was performed between AD and non AD groups. This analysis calculated specificity and a sensitivity around 74%.

Figure 5:
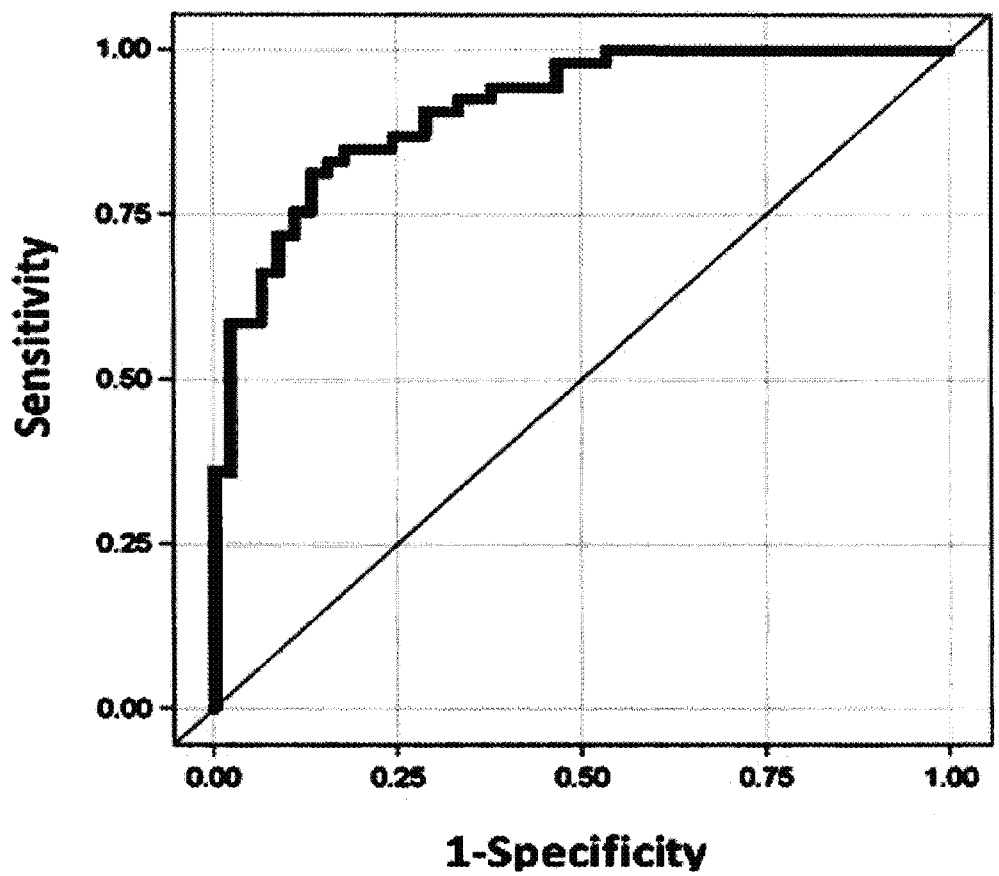
FIG. 5 shows the ROC curve obtained after logistical analysis of the results obtained with a cohort of 108 subjects (58 AD patients and 50 healthy controls or patients suffering non AD dementia. Two subsequent analyses were performed. During the first analysis influence diagnosis was also performed for each variable and this allowed outliers to be identified. Samples which were outliers for at least 2 variables were dropped out, i.e., 5 AD and 5 non AD. A new logistical regression analysis was then performed on a similar basis. The resulting ROC curve is illustrated in FIG. 5. This new analysis gave a sensitivity of 83% and a specificity of 82% (Table 4).

During this first analysis influence diagnosis was also performed for each variable and this allowed outliers to be identified. Samples which were outlier for at least 2 variables were dropped out, i.e., 5 AD and 5 non AD. A new logistical regression analysis was then performed on a similar basis. The resulting ROC curve is illustrated in FIG. 5. This new analysis gave a sensitivity of 83% and a specificity of 82% (Table 4).

TABLE 4

Characteristics of the ROC curve illustrated in FIG. 5

| Sensitivity | 83% |
|---|---|
| Specificity | 82% |
| Area under curve | 91% |

Conclusion:

This example shows that the primed binding of $A\beta_{1-42}$ on red blood cells can be used to detect Alzheimer's disease in human individuals with an unmatched specificity and sensitivity for such a peripheral test. These properties are in agreement with the general expectation of physician for this kind of test detecting AD. This also demonstrates its usefulness for diagnosis in clinical practice or for cohort recruitment of qualified patients in clinical studies.

Example 5

Use of a Combination of Aβ$_{1-42}$ Binding and PKC Conformation Changes Measurement to Detect Alterations in an Animal Model of Alzheimer Disease Methods:

Using the same animals as described in example 4, namely TAS/TPM transgenic mice and the wild type C57/BL6 mice sequential measurements of the Aβ$_{1-42}$ binding capacity on purified RBC were performed, using the protocol described in example 4 and of protein kinase C (PKC conformational changes using a specific probe derived from bis-indoyl maleimide coupled to a bodipy described in a previous patent (Patent FR0859098). The detailed protocol for this last measurement is described elsewhere (Janoshazi et al., 2006). The two biomarkers were measured either on a spectrofluorimeter or on a flow cytometer. After analysis, the values obtained for each biomarker were combined using a sum of squares equation when the measurement was performed on a spectrofluorimeter or by calculating their ratio when the measurement was performed on a flow cytometer.

Figure 6:
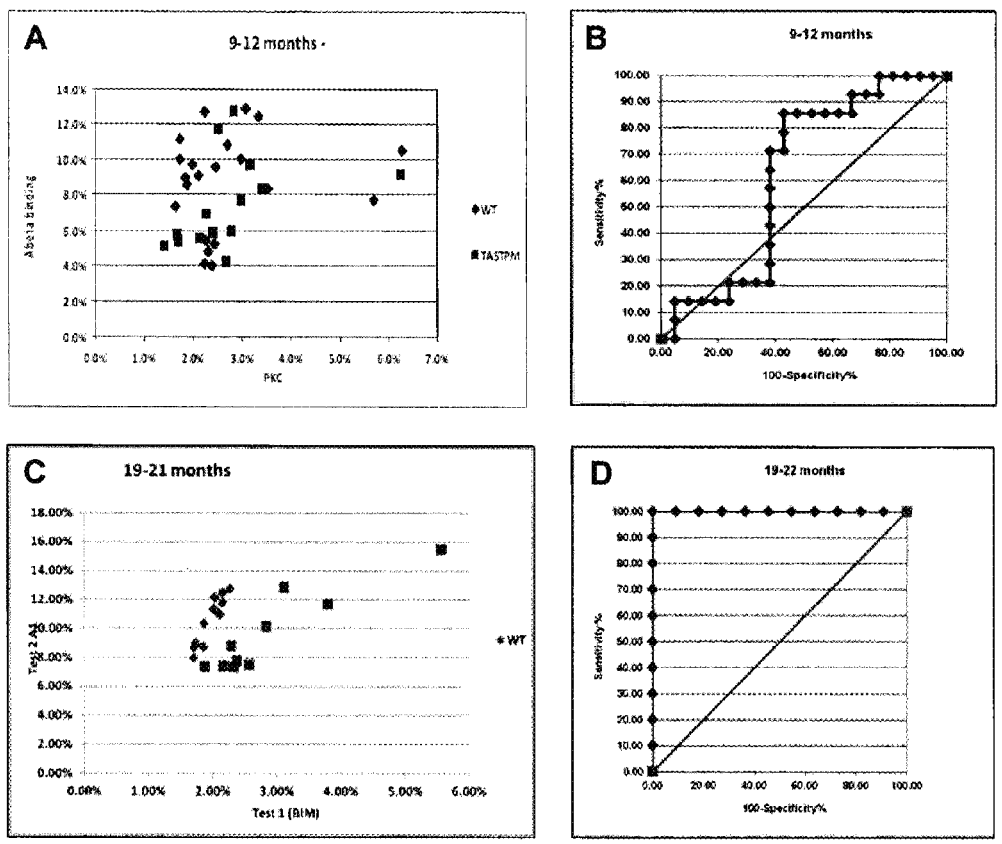
FIG. 6. An increased efficacy of the test in discriminating between wild type and transgenic animals was observed since at 20 months the separation of the two groups was complete as illustrated in FIG. 6: Combination of the assessment of PKC conformational change (abscissa) and $A\beta_{1-42}$ binding (ordinates) performed on red blood cells from TAS/TPM and wild type mice (panels A and C). Note that in animals aged 9-12 months (panel A) the discrimination between transgenic and control mice is incomplete, whereas a clear difference is observed in 20 month old mice (panel C). ROC curves were obtained by calculating the ratio between $A\beta_{1-42}$ binding and PKC conformation values for each sample (panels B and D). At 9-12 months (panel B) the sensitivity of the combination was 71.4% and the specificity was 62.2%. Both values were 100% in 20 month old animals (panel D).

Results:

An increased efficacy of the test in discriminating between wild type and transgenic animals was observed since at 20 months the separation of the two groups was complete as illustrated in FIG. 6: Combination of the assessment of PKC conformational change (abscissa) and Aβ$_{1-42}$ binding (ordinates) performed on red blood cells from TAS/TPM and wild type mice (panels A and C). Note that in animals aged 9-12 months (panel A) the discrimination between transgenic and control mice is incomplete, whereas a clear difference is observed in 20 month old mice (panel C). ROC curves were obtained by calculating the ratio between Aβ$_{1-42}$ binding and PKC conformation values for each sample (panels B and D). At 9-12 months (panel B) the sensitivity of the combination was 71.4% and the specificity was 62.2%. Both values were 100% in 20 month old animals (panel D).

Figure 7:
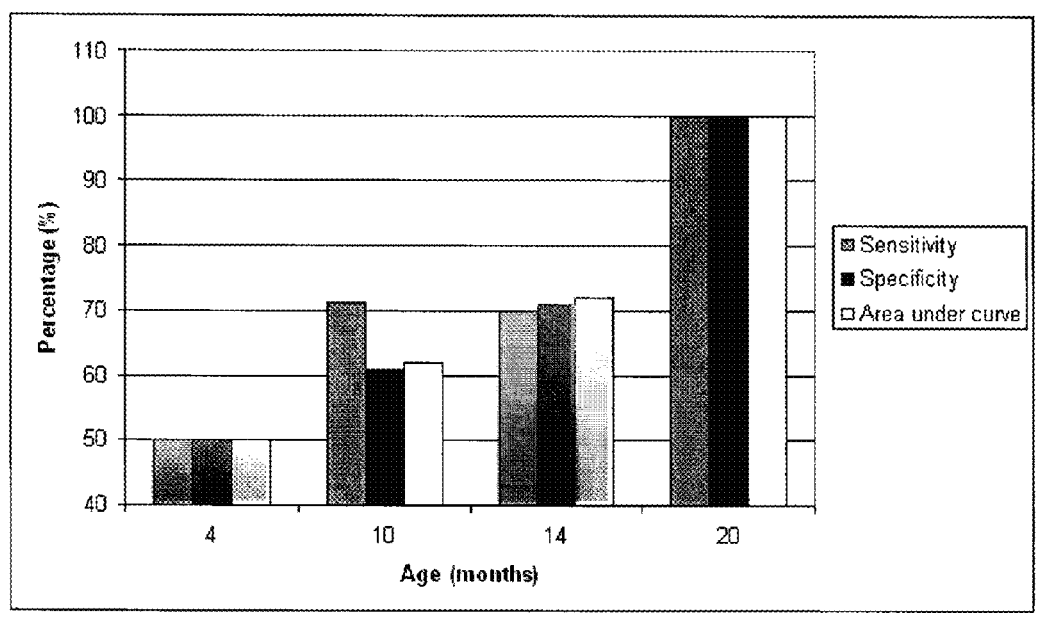
FIG. 7 further shows that combining $A\beta_{1-42}$ binding measurement and PKC conformational changes it is possible to accurately follow the disease progression. The tests were performed on TAS/TPM and wild type mice. The animals at 4 and 14 months were assessed on the spectrofluorimeter platform whereas at 10 and 20 months they were assessed on a flow-cytometer.

FIG. 7 further shows that combining Aβ$_{1-42}$ binding measurement and PKC conformational changes it is possible to accurately follow the disease progression. The tests were performed on TAS/TPM and wild type mice. The animals at 4 and 14 months were assessed on the spectrofluorimeter platform whereas at 9 and 20 months they were assessed on a flow-cytometer.

Conclusion:

In this example, the conformational change of PKC was used to detect AD. This biomarker is a functional biomarker complementary of primed Aβ$_{1-42}$ binding since the change in PKC occurs downstream the cascade of events induced by Aβ$_{1-42}$ binding to the cellular membrane (for a review see de Barry et al., 2009). The results show that combining the measurement of primed Aβ$_{1-42}$ binding with another complementary biomarker considerably increases the discriminative powerful of the test since a complete distinction of TAS/TPM mice versus Wild type mice was obtained in groups aged 20 months.

This example also shows that this combination of biomarkers efficiently reports on the disease progression in this animal model making possible to evaluate drug efficiency provide the target of these drugs is related to the physiopathology of the disease.

LIST OF REFERENCES

Arispe N. et al. (2010) Polyhistidine Peptide Inhibitor of the Aβ Calcium Channel Potently Blocks the Aβ-Induced Calcium Response in Cells. Theoretical Modeling Suggests a Cooperative Binding Process *Biochemistry* 49: 7847-7853.

Bateman D. A. and Chakrabartty A. (2009) Two Distinct Conformations of Aβ Aggregates on the Surface of Living PC12 Cells. *Biophys. J.* 96: 4260-4267.

Bateman D. A. and Chakrabartty A. (2011) Cell Surface Binding and Internalization of Aβ Modulated by Degree of Aggregation. *International J. Alz. Dis.* 2011, Article ID 962352, 13 pages.

Bezprozvanny I. (2009) Calcium signaling and neurodegenerative diseases. *Trends Mol Med* 15(3):89-100.

Braak H, Braak E. (1991) Demonstration of amyloid deposits and neurofibrillary changes in whole brain sections *Brain Pathol.* 1(3):213-6.

Brodaty H. et al (2011) The World of Dementia beyond 2020. *J Am Geriatr Soc.* 59(5):923-7.

Chin J H, et al. (2006). Beta-amyloid enhances intracellular calcium rises mediated by repeated activation of intracellular calcium stores and nicotinic receptors in acutely dissociated rat basal forebrain neurons. *Brain Cell Biol.*; 35(2-3): 173-86.

Chuang J Y et al (2012) Interactions between amyloid-beta and hemoglobin: Implication for Amyloid plaque formation in Alzheimer's disease. PLos One; 7(3):e33120.

Choi S R et al., (2012) Correlation of amyloid PET ligand florbetapin F18 binding with A beta aggregation and neuritic plaque deposition in postmorten brain tissue. *Alzheimer Dis assoc Disord* 2012 Jan:26(1):8-16.

Cizas P. et al. (2011) Prevention of amyloid-beta oligomer-induced neuronal death by EGTA, estradiol, and endocytosis inhibitor. *Medicina (Kaunas)* 47(2):107-12.

de Barry J, Liégeois C M, Janoshazi A (2010) Protein kinase C as a peripheral biomarker for Alzheimer's disease. *Exp Gerontol.* 45:64-9

Demuro A., et al. (2005) Calcium dysregulation and membrane disruption as a ubiquitous neurotoxic mechanism of soluble amyloid oligomers. *J Biol Chem* 280(17):17294-300.

Demuro A., et al. (2010). Calcium signaling and amyloid toxicity in Alzheimer disease. *J Biol. Chem.* 285(17):12463-8.

Funke S A et al. (2009) Detection of amyloid beta aggregates in body fluids a suitable method for a early diagnosis of Alzheimer's disease. *Curr Alzheimer res* 2009 jun;6(3): 285-9.

Frankfort S V et al., (2008) Amyloid beta protein and tau in cerebrospinal fluid and plasma as biomarkers for dementia: a review of recent literature. *Curr Clin pharmacol* 3(2) 123-31 review Gabelle A. et al., (2010) Correlations between soluble α/β forms of amyloid precursor protein and Aβ 38, 40 and 42 in human cerebrospinal fluid. *Brain res* 1357:135-83.

Georganopoulou D G et al (2005) Nanoparticule-based detection in cerebral spinal fluid of a soluble pathogenic biomarker for Alzheimer's disease. *Proc Natl Acad Sci USA.* 102(7):2263-4

Götz J et al. (2012) Tau-targeted treatment strategies in Alzheimer's disease. *British Journal of pharmacology;* 165(5): 1246-59.

Haes A J et al (2005) Detection of a biomarker for Alzheimer's disease from synthetic and clinical samples using a nanoscale optical biosensor. *J Am Chem Soc* 127(7):2264-71.

Hardy J. (2002) Testing times for the "amyloid cascade hypothesis". *Neurobiol Aging.* 23(6):1073-4.

Howlett D R et al (2004) Cognitive correlates of Abeta deposition in male and female mice bearing amyloid precursor protein and presenilin-1 mutant transgenes. *Brain Res;* 1017 . . . 130-136

Howlett D R et al. (2008) Abeta deposition and related pathology in an APPxPS1 transgenic mouse model of Alzheimer's disease. *Histol Histopathol.* 23(1):67-76.

Innocent N. et al. (2010) Oligomerisation differentially affects the acute and chronic actions of amyloid-β in vitro *Neuropharmacol.* 59: 343-352.

Jack C R Jr et al (2011) Alliance for aging research AD biomarkers work group: Structural MRI. *Neurobiol Aging* 32 Suppl1: S48-57 Review.

Jan A. et al. (2011) Aβ_42 Neurotoxicity Is Mediated by Ongoing Nucleated Polymerization Process Rather than by Discrete Aβ_42 Species. *J. Biol. Chem.* 286: 8585-8596.

Janoshazi A, et al. (2006) Alteration of protein kinase C conformation in red blood cells: A potential marker for Alzheimer's disease but not for Parkinson's disease. *Neurobiology of Aging,* 27: 245-251

Klein, W. L. et al. (2001) Targeting small Abeta oligomers: the solution to an Alzheimer's disease conundrum? *Trends Neurosci* 24:219-224.

Klein, W. L. (2002) Abeta toxicity in Alzheimer's disease: globular oligomers (ADDLs) as new vaccine and drug targets. *Neurochem Int* 41:345-352.

Klein, W. L. et al. (2004) Small assemblies of unmodified amyloid beta-protein are the proximate neurotoxin in Alzheimer's disease. *Neurobiol Aging* 25:569-580.

Krafft G. A. and Klein W. L. (2010) ADDLs and the signaling web that leads to Alzheimer's disease *Neuropharmacol.* 59: 230-242.

Kuo Y M, Kokjohn T A, Kalback W, Luehrs D, Galasko D R, Chevallier N, et al. 2000 Amyloid-beta peptides interact with plasma proteins and erythrocytes: implications for their quantitation in plasma. *Biochem. Biophys. Res. Comm.* 268, 750-756)

Marcus J N, Schachter J (2011) Targeting post-translational modifications on tau as a therapeutic strategy for Alzheimer's disease. *J Neurogenet.* 25(4): 127-33.

McManus A. et al. (2000) Enhancement of $^{45}Ca^{2+}$ Influx and Voltage-dependent $Ca^{2+}$ Channel Activity by □-Amyloid-(1-40) in Rat Cortical Synaptosomes and Cultured Cortical Neurons. *J. Biol. Chem.* 275: 4713-4718.

Nag S. et al. (2010) Measurement of the Attachment and Assembly of Small Amyloid-□Oligomers on Live Cell Membranes at Physiological Concentrations Using Single-Molecule Tools *Biophys. J.* 99: 1969-1975.

Nag S, et al. (2011) Nature of the amyloid-beta monomer and the monomer-oligomer equilibrium. *J Biol. Chem.* 286 (16): 13827-33.

Neniskyte U et al., (2011) Neuronal death induced by nanomolar amyloid β is mediated by primary phagocytosis of neurons by microglia. *J Biol. Chem.* 286(46):39904-13.

Pardon M C et al (2009) Repeated novel cage exposure-induced improvement of early Alzheimer's-like cognitive and amyloid changes in TASTPM mice is unrelated to changes in brain endocannabinoids levels. *Neurobiol Aging,* 30:1099-1113.

Pesini P et al. (2009) Evaluation of the □-amyloid pool in blood by ELISA sandwich is meaningful and reliable. 2d conference on Clinical Trials on Alzheimer's Disease, Las Vegas, USA, November 2009.

Poisnel G et al. (2012) PET imaging with [18F]AV-45 in an APP/PS1-21 murine model of amyloid plaque deposition. *Neurobiol Aging.* 23. [Epub ahead of print].

Ray S, et al. (2011) Tg2576 cortical neurons that express human A□ are susceptible to extracellular Aβ-induced, K+ efflux dependent neurodegeneration. *PLoS One.;* 6(4): e19026.

Rosén et al., (2012) Cerebrospinal fluid profiles and amyloid β-related biomarkers in alzheimer's disease. *Neuromolecular med* 14(1):65-73.

Selkoe, D. J. (2002) Deciphering the genesis and fate of amyloid beta-protein yields novel therapies for Alzheimer disease. *J Clin Invest JID*—7802877 110:1375-1381.

Selkoe, D. J. (2008) Soluble oligomers of the amyloid beta-protein impair synaptic plasticity and behavior. *Behav Brain Res* 192:106-113.

Suwalsky M et al (2009) Interaction between Alzheimer's amyloid-beta and amyloid-beta metal complexes with cell membranes. *J Alz Dis;* 17(1):81-90.

Tarawneh R. and Holtzman D. M. (2010) Biomarkers in translational research of Alzheimer's Disease *Neuropharmacol* 59: 310-322

Terry R D (2006) Alzheimer's disease and the aging brain. *J Geriatr Psychiatry Neurol.* 19(3):125-8. Review.

Other Background Art:

FR 97 09 823 (PCT appl no PCT/FR 98/01 660 and U.S. Pat. No. 6,703,212).

FR 05 01 515 5PCT appl no PCT/FR 06/000 332.

FR 05 01 518 (PCT appl n° PCT/FR 06/000 333B and U.S. Pat. No. 7,897,786).

FR 08 59 098 (PCT/FR 09/052 606).

FR 08 07 473 (PCT appl n° PCT/FR 09/001,486)

WO 2004/031400 A2. Amyloid beta-derived diffusible ligands (ADDLs), ADDL-surrogates, ADDL-binding molecules and issues thereof U.S. 2006/0228349 A1. Anti-ADDL antibodies and use thereof U.S. 2003/0068316 A1. Anti-ADDL antibodies and use thereof WO 2006/014478 A1. Monoclonal antybodies the target pathological assemblies of amyloid beta.

US 2006/0178302 A1. Amylois beta protein (globular assembly and use thereof).

WO 01/10900 A2. Amylois beta protein (globular assembly and use thereof).

WO 98/33815 A1, U.S. Pat. No. 6,218,506 B1. Amylois beta protein (globular assembly and use thereof).

U.S. 2006/0166275 A1. Amylois beta protein (globular assembly and use thereof).

MODIFICATIONS AND OTHER EMBODIMENTS

Various modifications and variations of the described biomarker complexes, compositions containing them, and methods of their use as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical, biological, chemical or pharmacological arts or related fields are intended to be within the scope of the following claims.

INCORPORATION BY REFERENCE

Each document, including any patent, patent application or patent publication, cited by or referred to in this disclosure is incorporated by reference in its entirety, especially with respect to the specific subject matter surrounding the citation of the reference in the text. However, no admission is made that any such reference constitutes background art and the right to challenge the accuracy and pertinence of any cited document is reserved.

The invention claimed is:

1. A complex comprising an isolated Aβ amyloid peptide and a cell or a cell membrane, wherein said complex is obtainable by incubating a cell or cell membrane with 0.1 to 2 micromolars of an isolated Aβ amyloid peptide in a biological fluid or an iso-osmotic medium and at a temperature ranging between 4 and 42° C.

2. The complex of claim 1, wherein said isolated Aβ amyloid peptide comprises at least six contiguous amino acids of Aβ1-42 of human, mouse or rat Aβ amyloid peptide of SEQ. ID. NOS: 1, 2 or 3, respectively.

3. The complex of claim 1, wherein said isolated Aβ amyloid peptide is selected in the group consisting of human Aβ1-42 of SEQ. ID. NO: 4, human Aβ1-40 of SEQ. ID. NO: 5, human Aβ17-25 of SEQ. ID. NO: 6 or Aβ25-35 of SEQ. ID. NO: 7.

4. The complex of claim 1, wherein said isolated Aβ amyloid peptide is tagged or labeled with a fluorophore, radioisotope, stable isotope, spin marker, enzyme, conjugated residue, or other detectable marker.

5. The complex of claim 1, wherein said cell or cell membrane is a mammalian cell or cell membrane selected from the group consisting of
   a red blood cell or red blood cell membrane;
   a platelet or platelet cell membrane;
   a non-RBC, non-platelet anuclear cell or the membrane of such an anuclear cell;
   white blood cell or white blood cell membrane; and
   a cell derived from the nervous system or a membrane of such a cell;
   an epithelial cell or membrane of epithelial cell; and
   a mucosal cell or a membrane of such a cell.

6. A method of diagnosing Alzheimer's disease or a disease or disorder associated with amyloid deposition comprising detecting the complex of claim 1 in a sample.

7. A method for identifying a therapeutic agent or compound for treating Alzheimer's disease or a disease or disorder characterized by amyloid deposits comprising:
   identifying an agent or compound that inhibits membrane priming by beta amyloid peptide or a molecule derived therefrom.

8. A composition or kit comprising at least one of:
   one or more reagents for incubating the cells or cell membranes with a tagged or labelled beta amyloid peptide or a molecule derived from a beta amyloid peptide,
   one or more reagents for measuring a complex of the labelled beta amyloid peptide or a molecule derived therefrom, with said cells or cell membranes,
   one or more reagents for isolating or purifying a cell or cell membrane to which a beta amyloid peptide has bound,
   a device to detect or quantify the amount of complex formation,
   software for detecting, quantifying or otherwise analyzing complex formation, and/or
   written instructions or a user manual for using the composition or kit to detect or assess the risk of Alzheimer's disease.

9. A method for detecting the presence of a complex of claim 1 comprising:
   a) purifying or isolating cells or cell membranes from a biological sample of a subject suspected of having, or at risk of developing, Alzheimer's disease or a disease characterized by deposits of amyloid protein in brain or nervous system,
   b) contacting the purified or isolated cells or cell membranes with a tagged or labeled Aβ amyloid peptide that comprises at least six contiguous amino acids of Aβ1-42 of a mammalian Aβ amyloid peptide at a concentration between 0.1 and 2 micromolars for a time and under conditions suitable for complex formation, said conditions include an iso-osmotic medium and a temperature comprised between 4 and 42° C. and an incubation time comprised between 10 minutes and 3 hours, and
   c) detecting complex formation between the cells or cell membranes and the labeled Aβ amyloid peptide by measuring tagged or labeled Aβ amyloid peptide bound to said cells or cell membranes.

10. The method of claim 9, further comprising:
    d) comparing the amount of complex formation to the amount of complex formation in a normal subject, in a subject not having Alzheimer's disease, or to a normal control value, and diagnosing the subject as having Alzheimer's disease or as being at risk of developing Alzheimer's disease when complex formation is higher than that in the normal subject, subject not having Alzheimer's disease, or normal control value.

11. The method of claim 9, wherein the subject is being treated for Alzheimer's disease or for a disease or disorder characterized by the deposit of amyloid.

12. A noninvasive method according to claim 9 for diagnosing a subject as having Alzheimer's disease or for being at risk of developing or progressing for Alzheimer's disease or a disease or disorder characterized by the deposit of amyloid in the brain or nervous system comprising:
    a) purifying or isolating cells from a biological sample of a subject suspected of having, or at risk of developing or progress to, Alzheimer's disease,
    b) contacting the purified or isolated cells with a tagged or labeled molecule sensitive to calcium concentration under conditions including an iso-osmotic medium temperature comprised between 4 and 42° C. and an exposure time, which allows said molecule to be loaded inside the cells,
    c) contacting the purified or isolated cells with an Aβ amyloid peptide that comprises at least six contiguous amino acids of Aβ1-42 of a mammalian Aβ amyloid peptide at a concentration between 0.1 and 2 micromolars for a time and under conditions sufficient for the Aβ amyloid peptide to modulate intracellular calcium concentration, said conditions include an iso-osmotic medium and a temperature comprised between 4 and 42° C.,
    d) detecting the intracellular calcium concentration in the cells contacted with the Aβ amyloid peptide by measuring said tagged or labeled molecule sensitive to calcium concentration,
    e) comparing the intracellular calcium concentration in the cells to that obtained by an otherwise identical method from sample obtained from a normal subject, a subject not having Alzheimer's disease, or to a normal control value, and
    f) diagnosing the subject as having Alzheimer's disease or as being at risk of developing or progressing for Alzheimer's disease when intracellular calcium concentration is higher than the intracellular calcium concentration determined for the normal subject, subject not having Alzheimer's disease, or normal control value.

13. A non-invasive method according to claim 12 wherein said Aβ amyloid peptide is tagged or labeled and wherein step d) also comprises the detection of complex formation between the cells and the tagged or labeled Aβ amyloid peptide by measuring tagged or labeled Aβ amyloid peptide bound to said cells.

14. A method according to claim 9 for screening an agent or compound that inhibits priming for use as a therapeutic agent for Alzheimer's disease or a disease or disorder characterized by amyloid deposits, comprising:
   a) isolating cells or cell membranes,
   b) contacting the isolated cells or cell membranes with an agent or compound to be tested and with 0, 1 to 100 nanomolars of an amyloid peptide under conditions sufficient to prime the cell or cell membrane of a control that is not contacted with the agent or test compound, wherein said amyloid peptide comprises at least six contiguous amino acids of Aβ1-42 of a mammalian Aβ amyloid peptide, said conditions include an iso-osmotic medium and a temperature comprised between 4 and 42° C. and an incubation time between 10 minutes and 24 hours,
   c) contacting the purified or isolated cells or cell membranes from step b) with a tagged or labeled Aβ amyloid peptide that comprises at least six contiguous amino acids of Aβ1-42 of a mammalian Aβ amyloid peptide at a concentration between 0.1 and 2 micromolars for a time and under conditions suitable for complex formation, said conditions include an iso-osmotic medium and a temperature comprised between 4 and 42° C.,
   d) detecting complex formation between the cells or cell membranes and the labeled Aβ amyloid peptide by measuring tagged or labeled Aβ amyloid peptide bound to said cells or cell membranes,
   e) comparing the amount of complex formation in the cells contacted with the agent or compound with the amount of complex formation in an otherwise identical control sample that was not contacted with the agent or compound, and
   f) selecting a compound that reduces complex formation compared to the control.

15. A method according to claim 14 for screening an agent or compound that inhibits the effects of priming for use as a therapeutic agent for Alzheimer's disease or a disease or disorder characterized by amyloid deposits, comprising:
   a) purifying or isolating cells or cell membranes,
   b) contacting the isolated cells or cell membranes with an agent or compound to be tested and with 0, 1 to 100 nanomolars of an amyloid peptide, under conditions sufficient to prime the cell or cell membrane, wherein said amyloid peptide comprises at least six contiguous amino acids of Aβ1-42 of a mammalian Aβ amyloid peptide, said conditions include an iso-osmotic medium and a temperature comprised between 4 and 42° C. and an incubation time between 10 minutes and 24 hours,
   c) contacting the purified or isolated cells or cell membranes from step b) with
      (i) a tagged or labeled Aβ amyloid peptide that comprises at least six contiguous amino acids of Aβ1-42 of a mammalian Aβ amyloid peptide for a time and under conditions suitable for complex formation, or
      (ii) contacting the purified or isolated cells with a tagged or labeled molecule sensitive to calcium concentration under conditions including an iso-osmotic medium temperature comprised between 4 and 42° C. and an exposure time, which allows said molecule to be loaded inside the cells and subsequently a concentration of Aβ amyloid peptide sufficient to cause an increase in intracellular calcium concentration of a control cell that was primed but not subsequently exposed to the test agent or test compound, wherein the amyloid peptide comprises at least six contiguous amino acids of Aβ1-42 of a mammalian Aβ amyloid peptide for a time and under conditions suitable for complex formation,
   d) detecting complex formation between the cells or cell membranes and the labeled Aβ amyloid peptide for (i), or detecting the intracellular calcium concentration of cells for (ii), or any parameter of the signaling cascade triggered by beta-amyloid peptide binding or intracellular calcium (iii)
   e) comparing the amount of complex formation in the cells contacted with the agent or compound with the amount of complex formation in an otherwise identical control sample that was not contacted with the agent or compound for (i); or comparing the intracellular calcium concentration in the cells to that obtained by an otherwise identical method from sample obtained from a normal subject, a subject not having Alzheimer's disease, or to a normal control value for (ii); or any parameter of the signaling cascade triggered by beta-amyloid peptide binding or intracellular calcium (iii) and
   f) selecting a test agent or test compound that reduces complex formation in (i) compared to the control; or that reduces intracellular calcium concentration in (ii), or any parameter of the signaling cascade triggered by beta-amyloid peptide binding or intracellular calcium (iii).

16. A non invasive method according to claim 9 for detecting alterations in a cell or a cell membrane of a circulating or peripheral cell induced by Alzheimer's disease or by a disease or disorder characterized by deposition of amyloid comprising:
   a) purifying or isolating cells or cell membranes from a biological sample of a subject suspected of having, or at risk of developing, Alzheimer's disease or a disease characterized by deposits of amyloid protein,
   b) contacting the purified or isolated cells or cell membranes with a tagged or labeled Aβ amyloid peptide that comprises at least six contiguous amino acids of Aβ1-42 of a mammalian Aβ amyloid peptide at a concentration between 0.1 and 2 micromolar for a time and under conditions suitable for complex formation, said conditions include an iso-osmotic medium and a temperature comprised between 4 and 42° C.,
   c) detecting complex formation between the cells or cell membranes and the labeled Aβ amyloid peptide by measuring tagged or labeled Aβ amyloid peptide bound to said cells or cell membranes, and
   d) in said isolated cells or cell membranes obtained in step b) measuring a change in the conformation of Protein Kinase C (PKC) or at least one other parameter associated with Alzheimer's disease or a disease or disorder characterized by deposition of amyloid.

17. A method according to claim 9 for developing an animal model for human Alzheimer's disease comprising:
   a) purifying or isolating cells or cell membranes from a biological sample of a test animal,
   b) contacting said purified or isolated cells or cell membranes with
      (i) a tagged or labeled Aβ amyloid peptide that comprises at least six contiguous amino acids of Aβ1-42 of a mammalian AR amyloid peptide for a time and under conditions suitable for complex formation, or
      (ii) a concentration of Aβ amyloid peptide sufficient to cause an increase in intracellular calcium concentration of a control cell that was primed, wherein the amyloid peptide comprises at least six contiguous amino acids of Aβ1-42 of a mammalian Aβ amyloid peptide for a time and under conditions suitable for complex formation, c) detecting complex formation between the cells or cell membranes and the labeled Aβ amyloid peptide for (i), or detecting the intracellular calcium concentration of cells for (ii) or any parameter of the signaling cascade triggered by beta-amyloid peptide binding or intracellular calcium (iii), d) comparing the amount of complex formation in the cells contacted with the agent or compound with the amount of complex formation in an otherwise identical sample obtained from a control animal, a subject not having Alzheimer's disease, or to a normal control value in (i); or comparing the intracellular calcium concentration in the cells to that obtained by an otherwise identical method from sample obtained from a normal animal, a subject not having Alzheimer's disease, or to a normal control value for (ii); and f) selecting a test animal which exhibits elevations in complex formation in cells compared to the control in (i); or that exhibits elevations in intracellular calcium concentration in cells compared to control cells in (ii) or any parameter of the signaling cascade triggered by beta-amyloid peptide binding or intracellular calcium (iii).

18. A compound identified by the method of claim 14.

19. A method for treating AD or a disease or disorder characterized by amyloid deposition comprising administering a compound identified by the method of claim 14 to a subject in need thereof.

* * * * *

```
                              SEQUENCE LISTING

<160> NUMBER OF SEQ ID NOS: 8

<210> SEQ ID NO 1
<211> LENGTH: 770
<212> TYPE: PRT
<213> ORGANISM: Homo sapiens

<400> SEQUENCE: 1

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
                35                  40                  45

Asn Gly Lys Trp Asp Ser Asp Pro Ser Gly Thr Lys Thr Cys Ile Asp
            50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
                115                 120                 125

Val Pro Asp Lys Cys Lys Phe Leu His Gln Glu Arg Met Asp Val Cys
                130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Asn Val Asp Ser Ala Asp Ala Glu Glu Asp Asp Ser Asp Val
                195                 200                 205

Trp Trp Gly Gly Ala Asp Thr Asp Tyr Ala Asp Gly Ser Glu Asp Lys
                210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Glu Ser Val Glu Glu Val Val Arg
                275                 280                 285

Glu Val Cys Ser Glu Gln Ala Glu Thr Gly Pro Cys Arg Ala Met Ile
                290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
```

```
                340             345             350
Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765
```

Gln Asn
    770

<210> SEQ ID NO 2
<211> LENGTH: 770
<212> TYPE: PRT
<213> ORGANISM: Rattus rattus

<400> SEQUENCE: 2

Met Leu Pro Ser Leu Ala Leu Leu Leu Ala Trp Thr Val Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Lys Leu Asn Met His Met Asn Val Gln
        35                  40                  45

Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Thr His Ile Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Ser Ile Asp Ser Ala Asp Ala Glu Glu Asp Asp Ser Asp Val
        195                 200                 205

Trp Trp Gly Gly Ala Asp Thr Asp Tyr Ala Asp Gly Glu Asp Lys
    210                 215                 220

Val Val Glu Val Ala Glu Glu Glu Val Ala Asp Val Glu Glu Glu
225                 230                 235                 240

Glu Ala Glu Asp Asp Glu Asp Val Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Val Ser Ser Gln Ser Leu Leu Lys Thr
            340                 345                 350

Thr Ser Glu Pro Leu Pro Gln Asp Pro Val Lys Leu Pro Thr Thr Ala

```
            355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
                420                 425                 430
Gln His Phe Gln Glu Lys Val Glu Ser Leu Glu Gln Glu Ala Ala Asn
            435                 440                 445
Glu Arg Gln Gln Leu Val Glu Thr His Met Ala Arg Val Glu Ala Met
450                 455                 460
Leu Asn Asp Arg Arg Arg Leu Ala Leu Glu Asn Tyr Ile Thr Ala Leu
465                 470                 475                 480
Gln Ala Val Pro Pro Arg Pro His His Val Phe Asn Met Leu Lys Lys
                485                 490                 495
Tyr Val Arg Ala Glu Gln Lys Asp Arg Gln His Thr Leu Lys His Phe
                500                 505                 510
Glu His Val Arg Met Val Asp Pro Lys Lys Ala Ala Gln Ile Arg Ser
            515                 520                 525
Gln Val Met Thr His Leu Arg Val Ile Tyr Glu Arg Met Asn Gln Ser
            530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
                580                 585                 590
Leu Met Pro Ser Leu Thr Glu Thr Lys Thr Thr Val Glu Leu Leu Pro
            595                 600                 605
Val Asn Gly Glu Phe Ser Leu Asp Asp Leu Gln Pro Trp His Pro Phe
610                 615                 620
Gly Val Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
                660                 665                 670
Ala Glu Phe Gly His Asp Ser Gly Phe Glu Val Arg His Gln Lys Leu
            675                 680                 685
Val Phe Phe Ala Glu Asp Val Gly Ser Asn Lys Gly Ala Ile Ile Gly
            690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
                740                 745                 750
Gln Gln Asn Gly Tyr Glu Asn Pro Thr Tyr Lys Phe Phe Glu Gln Met
            755                 760                 765
Gln Asn
    770
```

<210> SEQ ID NO 3
<211> LENGTH: 770
<212> TYPE: PRT
<213> ORGANISM: Mus musculus

<400> SEQUENCE: 3

Met Leu Pro Ser Leu Ala Leu Leu Leu Ala Ala Trp Thr Val Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Lys Leu Asn Met His Met Asn Val Gln
        35                  40                  45

Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Thr His Ile Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Ser Val Asp Ser Ala Asp Ala Glu Glu Asp Asp Ser Asp Val
        195                 200                 205

Trp Trp Gly Gly Ala Asp Thr Asp Tyr Ala Asp Gly Gly Glu Asp Lys
    210                 215                 220

Val Val Glu Val Ala Glu Glu Glu Val Ala Asp Val Glu Glu Glu
225                 230                 235                 240

Glu Ala Asp Asp Asp Glu Asp Val Glu Asp Gly Asp Glu Val Glu Glu
                245                 250                 255

Glu Ala Glu Glu Pro Tyr Glu Glu Ala Thr Glu Arg Thr Thr Ser Thr
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Val Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Val Ser Thr Gln Ser Leu Leu Lys Thr
            340                 345                 350

Thr Ser Glu Pro Leu Pro Gln Asp Pro Asp Lys Leu Pro Thr Thr Ala
        355                 360                 365

Ala Ser Thr Pro Asp Ala Val Asp Lys Tyr Leu Glu Thr Pro Gly Asp

```
              370                 375                 380
Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
                420                 425                 430

Gln His Phe Gln Glu Lys Val Glu Ser Leu Glu Gln Glu Ala Ala Asn
            435                 440                 445

Glu Arg Gln Gln Leu Val Glu Thr His Met Ala Arg Val Glu Ala Met
450                 455                 460

Leu Asn Asp Arg Arg Leu Ala Leu Glu Asn Tyr Ile Thr Ala Leu
465                 470                 475                 480

Gln Ala Val Pro Pro Arg Pro His His Val Phe Asn Met Leu Lys Lys
                485                 490                 495

Tyr Val Arg Ala Glu Gln Lys Asp Arg Gln His Thr Leu Lys His Phe
                500                 505                 510

Glu His Val Arg Met Val Asp Pro Lys Lys Ala Ala Gln Ile Arg Ser
            515                 520                 525

Gln Val Met Thr His Leu Arg Val Ile Tyr Glu Arg Met Asn Gln Ser
530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Val
                565                 570                 575

Leu Ala Asn Met Ile Ser Glu Pro Arg Ile Ser Tyr Gly Asn Asp Ala
                580                 585                 590

Leu Met Pro Ser Leu Thr Glu Thr Lys Thr Thr Val Glu Leu Leu Pro
                595                 600                 605

Val Asn Gly Glu Phe Ser Leu Asp Asp Leu Gln Pro Trp His Pro Phe
            610                 615                 620

Gly Val Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Gly His Asp Ser Gly Phe Glu Val Arg His Gln Lys Leu
            675                 680                 685

Val Phe Phe Ala Glu Asp Val Gly Ser Asn Lys Gly Ala Ile Ile Gly
            690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
            755                 760                 765

Gln Asn
770

<210> SEQ ID NO 4
```

<211> LENGTH: 42
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 5
<211> LENGTH: 40
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 6
<211> LENGTH: 9
<212> TYPE: PRT
<213> ORGANISM: Homo sapiens

<400> SEQUENCE: 6

Leu Val Phe Phe Ala Glu Asp Val Gly
1               5

<210> SEQ ID NO 7
<211> LENGTH: 11
<212> TYPE: PRT
<213> ORGANISM: Homo sapiens

<400> SEQUENCE: 7

Gly Ser Asn Lys Gly Ala Ile Ile Gly Leu Met
1               5                   10

<210> SEQ ID NO 8
<211> LENGTH: 42
<212> TYPE: PRT
<213> ORGANISM: Mus musculus x Rattus norvegicus

<400> SEQUENCE: 8

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40